(12) United States Patent
Protsenko et al.

(10) Patent No.: US 12,026,874 B2
(45) Date of Patent: Jul. 2, 2024

(54) SYSTEMS AND METHODS FOR DETECTION AND ANALYSIS OF POLYPS IN COLON IMAGES

(71) Applicant: Magentiq Eye LTD, Haifa (IL)

(72) Inventors: Yaroslav Protsenko, Kyiv (UA); Yuri Rapoport, Haifa (IL); Dror Zur, Haifa (IL)

(73) Assignee: Magentiq Eye LTD, Haifa (IL)

( * ) Notice: Subject to any disclaimer, the term of this patent is extended or adjusted under 35 U.S.C. 154(b) by 456 days.

(21) Appl. No.: 17/393,523

(22) Filed: Aug. 4, 2021

(65) Prior Publication Data

US 2023/0043645 A1 Feb. 9, 2023

(51) Int. Cl.
*G06T 7/00* (2017.01)
*G06T 7/60* (2017.01)
*G16H 30/40* (2018.01)
*G16H 50/20* (2018.01)

(52) U.S. Cl.
CPC .............. *G06T 7/0012* (2013.01); *G06T 7/60* (2013.01); *G16H 30/40* (2018.01); *G16H 50/20* (2018.01); *G06T 2200/24* (2013.01); *G06T 2207/10068* (2013.01); *G06T 2207/20081* (2013.01); *G06T 2207/30032* (2013.01)

(58) Field of Classification Search
CPC ......... G06T 7/0012; G06T 7/60; G16H 50/20; G16H 30/40
See application file for complete search history.

(56) References Cited

U.S. PATENT DOCUMENTS

| | | | |
|---|---|---|---|
| 2005/0008205 A1* | 1/2005 | Kiraly | H04N 13/128 382/128 |
| 2014/0010430 A1* | 1/2014 | Chandelier | A61B 6/5217 382/131 |
| 2018/0052165 A1* | 2/2018 | Wang | G01N 33/57419 |
| 2018/0225820 A1* | 8/2018 | Liang | G16H 20/40 |
| 2018/0253839 A1* | 9/2018 | Zur | A61B 1/000094 |
| 2021/0366593 A1* | 11/2021 | Takenouchi | G09G 5/373 |
| 2023/0007982 A1* | 1/2023 | Cherubini | G06T 7/73 |

OTHER PUBLICATIONS

Chaptini et al. "Variation in Polyp Size Estimation Among Endoscopists and Impact on Surveillance Intervals", Gastrointestinal Endoscopy, 80(4):652-659, Oct. 2014.

(Continued)

*Primary Examiner* — David Bilodeau

(57) ABSTRACT

There is provided a method, comprising: feeding 2D image (s) of an internal surface of a colon captured by an endoscopic camera, into a machine learning model, wherein the 2D image(s) excludes a depiction of an external measurement tool, wherein the machine learning model is trained on records, each including 2D images of the internal surface of the colon of a respective subject labelled with ground truth labels of respective bounding boxes enclosing respective polyps and at least one of an indication of size and a type of the respective polyp indicating likelihood of developing maligiancy, obtaining a bounding box for a polyp and at least one of an indication of size and type of the polyp, and generating instructions for presenting within the GUI, an overlay of the bounding box over the polyp and the at least one of the indication of size and type of the polyp.

29 Claims, 10 Drawing Sheets

(56) References Cited

OTHER PUBLICATIONS

Ferlitsch et al. "Colorectal Polypectomy and Endoscopic Mucosal Resection (EMR): European Society of Gastrointestinal Endoscopy (ESGE) Clinical Guideline", Endoscopy, 49(03):270-297, 2017.
Gopalswarmy et al. "Is in Vivo Measurement of Size of Polyps Puring Colonoscopy Accurate?" Gastrointestinal Endoscopy,46(6):497-502, Dec. 1997.
Hassan et al. "Post Polypectomy Colonoscopy Surveillance: European Society of Gastrointestinal Endoscopy (ESGE) Guideline—Update 2020", Endoscopy 52(08): 687-700, 2020.
Kim et al. "Is Forceps More Useful Than Visualization for Measurement of Colon Polyp Size?" World Journal of Gastroenterology, 22(11):3220-3226, Mar. 21, 2016.
Morales et al. "The Difference in Colon Polyp Size Before and After Removal", Gastrointestinal Endoscopy, 43(1):25-28, Jan. 1996.
Suykens et al. Automated Polyp Size Estimation With Deep Learning Reduces Interobserver Variability. Gastrointest Endoscopy, 91(6):241-242, Jun. 1, 2020.
VTM Technologies VTM Technologies—Measurement Made Easy,Jan. 29, 2021.

\* cited by examiner

SYSTEMS AND METHODS FOR DETECTION AND ANALYSIS OF POLYPS IN COLON IMAGES

FIELD AND BACKGROUND OF THE INVENTION

The present invention, in some embodiments thereof, relates to colonoscopy and, more specifically, but not exclusively, to machine learning models for detection and analysis of polyps from colon images captured during a colonoscopy procedure.

Colonoscopy is the gold standard for detection and removal of colonic polyps. During colonoscopy, a long flexible tube called a colonoscope is advanced within the colon. A video camera at the end of the colonoscope captures images, which are presented on a display to the physician. The physician examines the internal surface of the colon for the presence of polyps. Identified polyps are removed using instruments of the colonoscope. Early removal of cancerous polyps may eliminate or reduce risk of colon cancer.

SUMMARY OF THE INVENTION

According to a first aspect, a computer implemented method of generating instructions for presenting a graphical user interface (GUI) for dynamically evaluating at least one polyp in a plurality of endoscopic images of a colon of a subject, comprises: feeding at least one 2D image of an internal surface of a colon captured by an endoscopic camera located within a lumen of the colon, into a machine learning model, wherein the at least one 2D image excludes a depiction of an external measurement tool, wherein the machine learning model is trained on a training dataset of a plurality of records, each record including 2D images of the internal surface of the colon of a respective subject labelled with ground truth labels of respective bounding boxes enclosing respective polyps and at least one of an indication of size and a type of the respective polyp indicating likelihood of developing malignancy, obtaining as an outcome of the machine learning model, a bounding box for a polyp and at least one of an indication of size and type of the polyp, and generating instructions for presenting within the GUI, an overlay of the bounding box over the polyp and the at least one of the indication of size and type of the polyp.

According to a second aspect, a computer implemented method for training a machine learning model for polyp detection, comprises: creating a training dataset including a plurality of records, each record including a 2D image of a respective internal surface of a respective colon of a respective subject captured by an endoscopic camera located within a respective lumen of the respective colon, and at least one ground truth labels including at least one bounding box enclosing the respective polyp and at least one of the size and a type of the respective polyp indicating likelihood of developing malignancy, and training a machine learning model on the training dataset for generating a target bounding box over a target polyp and at least one of the indication of size and type of the polyp, in response to an input of a target 2D image.

According to a third aspect, a system for dynamically evaluating at least one polyp in a plurality of endoscopic images of a colon of a subject, comprises: at least one local device comprising: a first interface for connecting to an endoscopic camera, a second interface for connecting to a server, and at least one processor executing a code for obtaining at least one 2D image of an internal surface of a colon captured by the endoscopic camera located within a lumen of the colon, transmitting the at least one 2D image to the server over a network, receiving an indication of an overlay denoting at least one of: detection of at least one polyp, estimation of a size of the at least one polyp, and estimation of a type of the at least one polyp, and presenting the overlay on the at least one 2D image on display, and the server comprising: at least one processor executing a code for: feeding the at least one 2D image into a machine learning model, wherein the at least one 2D image excludes a depiction of an external measurement tool, wherein the machine learning model is trained on a training dataset of a plurality of records, each record including 2D images of the internal surface of the colon of the respective subject labelled with ground truth labels of respective bounding boxes enclosing respective polyps and at least one of an indication of size and a type of the respective polyp indicating likelihood of developing malignancy, obtaining as an outcome of the machine learning model, at least one bounding box indicating the detection of the at least one polyp and at least one of an indication of size and type of the at least one polyp, and generating instructions fir presenting within the GUI, the overlay of the bounding box over the at least one polyp and the at least one of the indication of size and type of the at least one polyp.

In a further implementation form of the first, second, and third aspects, further comprising evaluating the at least one of the indication of size and type of the polyp using a set of rules, and generating instructions within the GUI for at least one of: removal of the polyp, tool and/or removal approach for removal of the polyp, and leaving the polyp in situ.

In a further implementation form of the first, second, and third aspects, further comprising excising the polyp when the at least one of the indication of size and type of the polyp meets a set of rules.

In a further implementation form of the first, second, and third aspects, further comprising feeding the overlay of the bounding box over the polyp and the at least one of the indication of size and type of the polyp into a treatment machine learning model to obtain an outcome indicating whether the polyp is to be removed or left in situ, the treatment machine learning model trained on a training dataset that includes multiple records, each record including a respective outcome of a sample bounding box over a sample polyp and the at least one of the indication of size and type of the sample polyp obtained from the machine learning model in response to a sample at least one 2D image, labelled with a ground truth indicating whether the sample polyp was removed or left in site.

In a further implementation form of the first, second, and third aspects, the machine learning model computes a plurality of feature maps for each 2D images, and generates a plurality of size maps for the plurality of feature maps, each respective size map including at least one 1-dimensional vector representing a logarithm of the estimated size of the polyp, wherein the logarithm of the estimated size is converted to the size using an exponentiation base that is an adjustable hyperparameter, wherein the exponentiation base is set to different values for different size maps computed from different feature maps, wherein the smaller the feature map the larger the exponentiation base.

In a further implementation form of the first, second, and third aspects, the machine learning model is implemented as a neural network, comprising a feature extractor component, a box coordinate network component, a confidence network component, and at least one of a size estimation component and a polyp type estimation component, wherein the feature extractor component generates a plurality of features maps in response to an input of an image, wherein the box coordinate network component generates coordinate maps indicating coordinates of candidate bounding boxes when applied to each respective feature map, wherein the confidence network component generates confidence maps indicating an estimated probability of a respective pixel being a detected polyp when applied respectively to each feature map, wherein the size estimation component generates size maps indicating an estimated polyp size When applied to each respective feature map, wherein the polyp type estimation component generates polyp type maps indicating a polyp type when applied to each respective feature map, wherein the bounding box is obtained by stacking the coordinates maps, the confidence maps, the size maps, and the polyp type maps.

In a further implementation form of the first, second, and third aspects, further comprising: feeding a plurality of 2D images into the machine learning model to obtain a plurality of bounding boxes and a plurality of indications of size and/or type, identifying a sequence of overlap between the plurality of bounding boxes, obtaining the plurality of indications of size and/or type over a selected time interval, removing outlier indications, averaging the plurality of indications of size and/or type to obtain a single size and/or single type, iterating the feeding, the identifying, the obtaining, the removing and the average, to obtain a scalar value for a next single size and/or type, when the scalar value for the next single size and/or type is higher by a margin than a previously computed single size and/or single type, selecting the higher scalar value as the outcome.

In a further implementation form of the first, second, and third aspects, feeding comprises sequentially feeding a plurality of 2D images into the machine learning model to obtain a plurality of bounding boxes and indication of size and/or type of the polyp, and switching the size and/or type of the polyp from a previous value to a new value when a number of consecutive bounding boxes above a predefined threshold are associated with the new value.

In a further implementation form of the first, second, and third aspects, feeding comprises sequentially feeding a plurality of 2D images into the machine learning model to obtain a plurality of bounding boxes and indication of size and/or type of the polyp, and further comprising: generating a plurality of records for the plurality of 2D images, each record of each respective 2D image including coordinates of the respective bounding box, a unique box ID assigned for each box associated with each unique polyp, a last seen parameter identifying a frame ID of a last 2D image of the plurality of 2D images where the unique box ID last appeared, wherein in response to a new unique box ID of a new box of a new 2D image: searching for at least one record of a previous box that overlaps with the new box by having an intersection over union (IoU) less than a threshold, setting the unique box ID of the new box to the value of the unique box ID of the previous box that overlaps with the new box, when no record is found in the search, assigning a new value to the unique box ID of the new box, removing records that have an overlapping box in the new 2D image, and creating new records for boxes of the new 2D image, removing records for which the last seen parameter is smaller than the frame ID of the new 2D image by a predefined constant.

In a further implementation form of the first, second, and third aspects, the at least one record of the previous box that overlaps with the new box is found when at least one of: (i) the previous box overlaps with the new box by having an intersection over union (IoU) less than a threshold, and (ii) tracking each box in the plurality of records and comparing new boxes against a tracked value of the boxes in the plurality of records, wherein the tracked values are computed by a tracking process that is fed an input of a current image, a bounding box of a polyp depicted in the current image, and a subsequent next image, and generates an outcome of an estimate of the bounding box for the polyp on the next frame, wherein the tracking value indicates an adjustment of coordinates of the bounding box of a current frame for the next frame.

In a further implementation form of the first, second, and third aspects, the at least 2D image is fed into a first machine learning model that generates a first bounding box over the polyp and the indication of size and into a second machine learning model that generates a second bounding box over the polyp and the indication of type, the first and second machine learning models running on a first processor, finding overlapping first and second bounding boxes having an IoU below a threshold by the first processor, and providing one of the first and second bounding boxes that are overlapping to a second processor for creation of the plurality of records.

In a further implementation form of the first, second, and third aspects, further comprising designating a dominant machine learning model and a non-dominant machine learning model from the first and second machine learning models, running the dominant machine learning model on the first processor and providing the bounding box outcome of the dominant machine learning model to the second processor, and in parallel running the non-dominant machine learning model and the identifying on the first processor, and providing the one of the first and second bounding boxes to the second processor.

In a further implementation form of the first, second, and third aspects, the indication of size comprises a scalar value, further comprising converting the scalar value to a range computed to cover a selected percentage of ground truth sizes in the training dataset.

In a further implementation form of the first, second, and third aspects, the range is a half-open range when insufficient ground truth is available in the training dataset to obtain an accurate estimation above a threshold.

In a further implementation form of the first, second, and third aspects, generating instructions comprises presenting the indication of size and/or type external to borders of the 2D image.

In a further implementation form of the first, second, and third aspects, when two or more different bounding boxes are generated for a single 2D image, the indication of size and/or type is presented for a single bounding box closest to a center of the single 2D image, and no indication of size and/or type is presented for other boxes located further away from the center than the single bounding box.

In a further implementation form of the first, second, and third aspects, generating instructions comprises presenting the bounding box with a color and/or border style by applying a set of rules to the indication of size and/or type.

In a further implementation form of the first, second, and third aspects, generating instructions comprises presenting the bounding box with one of: a first color when the type is adenoma, a second color when the type is non-adenoma, and a third color when the type is unknown.

In a further implementation form of the first, second, and third aspects, generating instructions comprises presenting the bounding box with a color hue according to estimated probability of type.

In a further implementation form of the first, second, and third aspects, further comprising: obtaining the at least one 2D image by a local device connected to the endoscopic camera, transmitting the at least one 2D image by the local device to a server over a network, wherein the feeding, the obtaining, and the generating instructions are performed by the server, and presenting on a local display associated with the endoscopic camera, the overlay within the GUI according to the instructions generated by the server and transmitted over the network.

In a further implementation form of the first, second, and third aspects, further comprising computing, a logarithm of the size of the respective polyp, wherein the size included in the records of the training dataset comprises the logarithm of the size.

In a further implementation form of the first, second, and third aspects, further comprising, in response to obtaining a plurality of target bounding boxes in response to feeding a plurality of target 2D images into the machine learning model, converting the logarithm of the size to a size, by using a set exponentiation base raised to the power of the logarithm of the size.

In a further implementation form of the first, second, and third aspects, the exponentiation base is a set hyper-parameter, the exponentiation base is different for different size maps generated from different feature maps, wherein a relatively smaller feature map is associated with a relatively larger exponentiation base and a relatively larger feature map is associated with a relatively smaller exponentiation base.

In a further implementation form of the first, second, and third aspects, each record of the training dataset includes ground truth labels for the size and type of the respective polyp.

In a further implementation form of the first, second, and third aspects, the machine learning model includes a size head portion and a type head portion, and during training a single loss function that optimizes the size head portion and the type head portion simultaneously is used.

In a further implementation form of the first, second, and third aspects, 2D images of the records are further associated with a was-noticed parameter indicating whether the respective polyp was noticed by the user performing the procedure and a was-treated parameter indicating whether the respective polyp was removed, and automatically assigning the ground truth label indicating type of polyp to non-adenoma when the was-noticed parameter indicates true and the was-treated parameter indicates false.

In a further implementation form of the first, second, and third aspects, at least one of: (i) automatically assigning the was-noticed parameter to true when the respective polyp is approximately in the middle of the 2D image for at least a selected duration of time, (ii) automatically assigning the was-noticed parameter to false when the respective polyp does not appear approximately in the middle of the image for at least the selected duration of time, (iii) automatically assigning the was-treated parameter to true when a treatment tool appears in the 2D image while a respective polyp is approximately in the middle of the 2D image, and (iv) automatically assigning the was-treated parameter to false when no treatment tool appears in the 2D image while the respective polyp is approximately in the middle of the 2D image.

In a further implementation form of the first, second, and third aspects, the indication includes size, and training for size is performed with a loss function that includes pixel-wise root mean square error (RMSE) between ground truth size maps and machine learning model generated size maps by considering map pixels correspond to ground truth bounding boxes encompassing respective polyps, wherein during training the ground truth and size maps include a logarithm of the size.

In a further implementation form of the first, second, and third aspects, the indication further includes type, and training is performed for size and for type, wherein training is performed for type using a divergence metric.

In a further implementation form of the first, second, and third aspects, the machine learning model is trained on a central computing device, and copies of the machine learning model when trained are distributed to each of a plurality of servers for inference of 2D images obtained from respective associated local devices.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
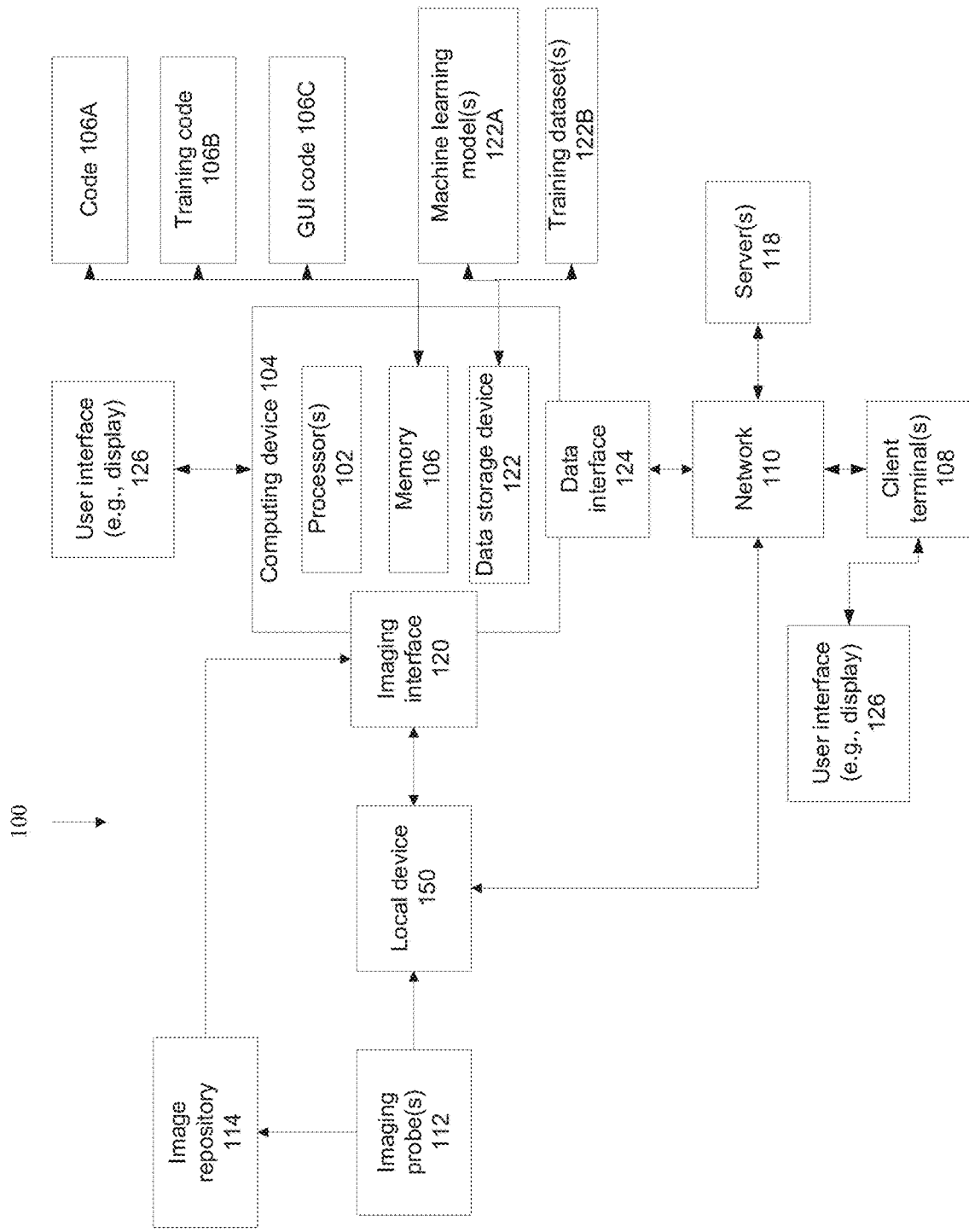
FIG. 1 is a block diagram of components of a system for training a machine learning model and/or for using the trained machine learning model for estimating size and/or type of polyps depicted in images acquired by a camera located on an endoscope within a colon of a target patient, in accordance with some embodiments of the present invention.

The present invention, in some embodiments thereof, relates to colonoscopy and, more specifically, but not exclusively, to machine learning models for detection and analysis of polyps from colon images captured during a colonoscopy procedure.

An aspect of some embodiments of the present invention relates to systems, methods, an apparatus (e.g., computing device), and/or code instructions (e.g., stored on a memory and executable by one or more hardware processors) for presenting a graphical user interface (GUI) indicating a size and/or type (e.g., adenoma, non-adenoma, unknown) of one or more polyps depicted in endoscopic images of a colon of a subject. A 2D image(s) of an internal surface of a colon captured by an endoscopic camera located within a lumen of the colon (e.g., captured during a colonoscopy procedure) is into a trained machine learning (ML) model(s). The 2D image excludes a depiction of an external measurement tool, for example, a standard measurement tool used as a known size reference for estimating a size of the polyp. The size and/or type of the polyp may be estimated from images of the colon alone, without use of external instruments within known sizes as additional aids. A bounding box delineating a polyp and an indication of size and/or type of the polyp is obtained as an outcome of the machine learning model(s). Optionally, both size and type of the polyp are obtained as outcomes of a single ML model which is trained on records of images labelled with ground truth labels of boundary boxes, size, and type, for each polyp. Instructions for presenting an overlay of the bounding box over the polyp and the indication of size and/or type of the polyp within the GUI, are generated. Recommendations for treatment of the detected polyp may he automatically generated according to the size and/or type. The polyp may be treated according to the estimated size and/or type.

An aspect of some embodiments of the present invention relates to systems, methods, an apparatus (e.g., computing device), and/or code instructions (e.g., stored on a memory and executable by one or more hardware processors) for training one or more MIL model(s) for estimating a size and/or type of a polyp and generating a bounding box delineating a detected polyp in response to one or more target 2D images depicting an internal surface of a colon of a subject. Optionally, a single ML model is trained to generate outcomes of both the size and type of the polyp. For training the single ML model, a training dataset of multiple records is created, Each record includes a 2D image(s) of a respective internal surface of a respective colon of a respective subject captured by an endoscopic camera located within a respective lumen of the respective colon, and ground truth labels including a bounding box enclosing the respective polyp, a size of the polyp, and a type of the polyp (e.g., indicating likelihood of developing malignancy, for example, adenoma, non-adenoma, and unknown). Alternatively, when two ML models are trained, each ML model may be trained on a different training dataset, that may share the same 2D images and bounding boxes ground truth labels. One training dataset for training a first ML model further includes the ground truth label of size for generating an outcome of the size of the polyp, and another training dataset for training a second ML model further includes the ground truth label of type for generating an outcome of the type of the polyp.

At least some implementations of the systems, methods, apparatus, and/or code instructions described herein relate to the medical problem of treating a patient, in particular, for identifying and removing polyps likely to develop into cancer from within a colon of a patient. Polyps are abnormal growths rising from the lining of the colon that protrude into the lumen. Polyps are common, especially as people get older, Some polyps may develop into cancer. Early detection and removal of the polyps, such as during a screening colonoscopy, reduces or prevents cancer. Since removal of polyps poses a risk to the patient, such as perforation of the colon and/or excessive bleeding, a decision of whether to remove each identified polyp is made rather than removing all polyps by default. Polyps which are not at risk of developing into cancer may be left intact. Polyps at risk of developing into cancer should be removed. Large polyps increase risk of perforating the colon wall and/or increase risk of excessive bleeding, and therefore may not necessarily be removed during colonoscopy, but may be referred to other removal approaches such as surgery. Moreover, different sized polyps may require removal using different tools and/or different approaches. For example, the guidelines for the use colorectal polypectomy tools were outlined by ESGE in 2017, for example, as described with reference to Ferlitsch M, Moss A, Hassan C, et al. *Colorectal polypectomy and endoscopic mucosal resection* (*EMR*): *European Society of Gastrointestinal Endoscopy* (*ESGE*) *Clinical Guideline. Endoscopy.* 2017; 49(3):270-297. doi: 10.1055/s-0043-102569, incorporated herein by reference in its entirety. The ESGE recommends as first line tools:

Cold snare polypectomy (CSP) for polyps less than 5 millimeters (mm) in size.

CSP for sessile polyps 6-9 mm in size.

Hot snare polypectomy for polyps 10-19 mm in size.

Cold biopsy forceps are considered a second-line option for less than 3 mm sized polyps or when CSP is technically difficult.

At least some implementations of the systems, methods, apparatus, and/or code instructions described herein relate to the technical problem of providing automated assistance to a user to help evaluate detected polyps and/or select polyps for removal, and/or select the tool and/or removal approach for polyps selected for removed. In at least some implementations the technical solution is based on machine learning models and/or a GUI that estimate and present polyp size and/or characteristics of polyps (e.g., adenoma versus non-adenoma), optionally in real time during the colonoscopy procedure. The indication of polyp size and/or polyp characterization is designed to reduce and/or avoid interference with the colonoscopy procedure. The polyp size may be estimated using only captured images, without necessarily using an external reference tool that is passed through the colonoscope, such as open biopsy forceps or snare.

At least some implementations of the systems, methods, apparatus, and/or code instructions described herein improve the technical field of machine learning models and/or a GUI, by providing machine learning models and/or GUIs that estimate and present polyp size and/or characteristics of polyps, optionally in real time during the colonoscopy procedure, such as to assist the user in selecting which polyps to remove and which polyps to leave, and for polyps being removed, which removal approach and/or tool to use. The indication of polyp size and/or polyp characterization is designed to reduce and/or avoid interference with the colonoscopy procedure. The polyp size may be estimated using only captured images, without necessarily using an external reference tool that is passed through the colonoscope, such as open biopsy forceps or snare. Size of polyps may be estimated, for example, at the level of less than about 1-2 millimeter (mm) error.

Polyp size estimation is a new recommendation as part of the ESGE 2020 Post-polypectomy colonoscopy surveillance guidelines, for example, as described with reference to Hassan C, Antonelli G, Dumonceau J M, et al. *Post-polypectomy colonoscopy surveillance: European Society of Gastrointestinal Endoscopy (ESGE) Guideline—Update 2020*. Endoscopy. 2020; 52(8):687-700. doi:10.1055/a-1185-3109, incorporated herein by reference in its entirety. Standard clinical practice is for the physician to manually estimate the polyp size. However, Chaptini et al. have shown that polyp sizing based solely on visual estimation have been shown to be greatly over and under-estimated, for example, as described with reference to Chaptini L, Chaaya A, Depalma F, Hunter K, Peikin S, Laine L. *Variation in polyp size estimation among endoscopists and impact on surveillance intervals*. Gastrointest Endosc. 2014 October; 80(4): 652-659. doi: 10.1016/j.gie.2014.01.053. Epub 2014 Mar. 27. PMID: 24679658, incorporated herein by reference in its entirety. Thus, the guidelines suggest visual estimation bias can be reduced using a reference standard such as an open biopsy forceps or snare. However, using such reference standards is cumbersome, since it involved inserting another tool into the colonoscope and opening the tool inside the colon, may involve trying different tools of different fixed sizes until the right sized tools is found (which takes time, is cumbersome, and increases risk of injury to the patient) which may increase risk of injury to the internal colon wall, takes time to perform especially if there are multiple polyps, is still not fully accurate since the user still needs to estimate size relative to the tool, and/or increases risk of error such as mixing up measurement for nearby polyps.

Using standard approaches, polyp size and/or polyp type are measured after the polyps has been excised from the colon. Polyp size may be measured using a rule after the excision, for example, as described with reference to Gopalswamy N, Shenoy V N, Choudhry U, et al. *Is in vivo measurement of size of polyps during colonoscopy accurate? Gastrointest Endosc.* 1997; 46(6):497-502. doi: 10.1016/s0016-5107(97)70003-8, incorporated herein by reference in its entirety. However, such post-excision measurement is prone to error, since when excising using biopsy forceps the excised specimen is a "bite" taken of the polyp and might present an underestimation of the polyp size in vivo, for example, as described with reference to Morales T G, Sampliner R E, Garewal H S, Fennerty M B, Aickin M. *The difference in colon polyp size before and after removal. Gastrointest Endosc.* 1996; 43(1):25-28. doi: 10.1016/s0016-5107(96)70255-9, incorporated herein by reference in its entirety, showed the biopsy forceps as a measurement method with a tendency to overestimation (the polyps were also excised with the forceps). Kim J H, Park Si, Lee J H et al. *Is forceps more useful than visualization for measurement of colon polyp size? World J Gastroenterol.* 2016; 22(11): 3220-3226 doi:10.3748/wjg.v22.i11.3220, incorporated herein by reference in its entirety, tested in vivo estimation using a specific biopsy forceps (Radial Jaw 4 Biopsy Forceps, Boston Scientific, United States), tested against a measurement based on graduated catheter as a gold standard. The fully opened biopsy forceps measured 6 mm. A 10% increase in measurement accuracy was shown using a fully opened biopsy forceps versus visual estimation without aids (p<0.001). However, using fully opened biopsy forceps has several limitations, as discussed above. Cold snare is shown less frequently in the medical literature as an in vivo measurement tool. This is possibly due to the large variety of sizes available for snares, and the fact it is harder to make sure it is fully opened. Snares exists in various sizes ranging from 10 to 33 mm in width when fully dilated tool.

Polyp type may be determined by a pathologist looking at the cells of the removed polyp under a microscope.

Other technological approaches to estimate polyp size include, for example, Suykens J, Eelbode T, Daenen J, Suetens P, Macs F, Bisschops R. *Automated Polyp Size Estimation With Deep Learning Reduces Interobserver Variability. Gastrointest Endosc.* 2020 June; 91(6):supp. AB241-242. doi: 10.1016/j.gie.2020.03.1787, incorporated herein by reference in its entirety, from the medical imaging research center that infers polyps size based on biopsy forceps as a reference tool in the endoscopic image. Another approach, for example, as described with reference to VTM technologies Ltd. Website. Accessed Jan. 29, 2021. https:// www(dot)vtm-tech(dot)com/, incorporated herein by reference in its entirety, is based on using a laser line that is meant to be used as a virtual tape measure, based on a tool inserted through the endoscope's working channelix. In contrast, at least some implementations described herein do not rely on the presence of a reference tool that requires insertion through the endoscope.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
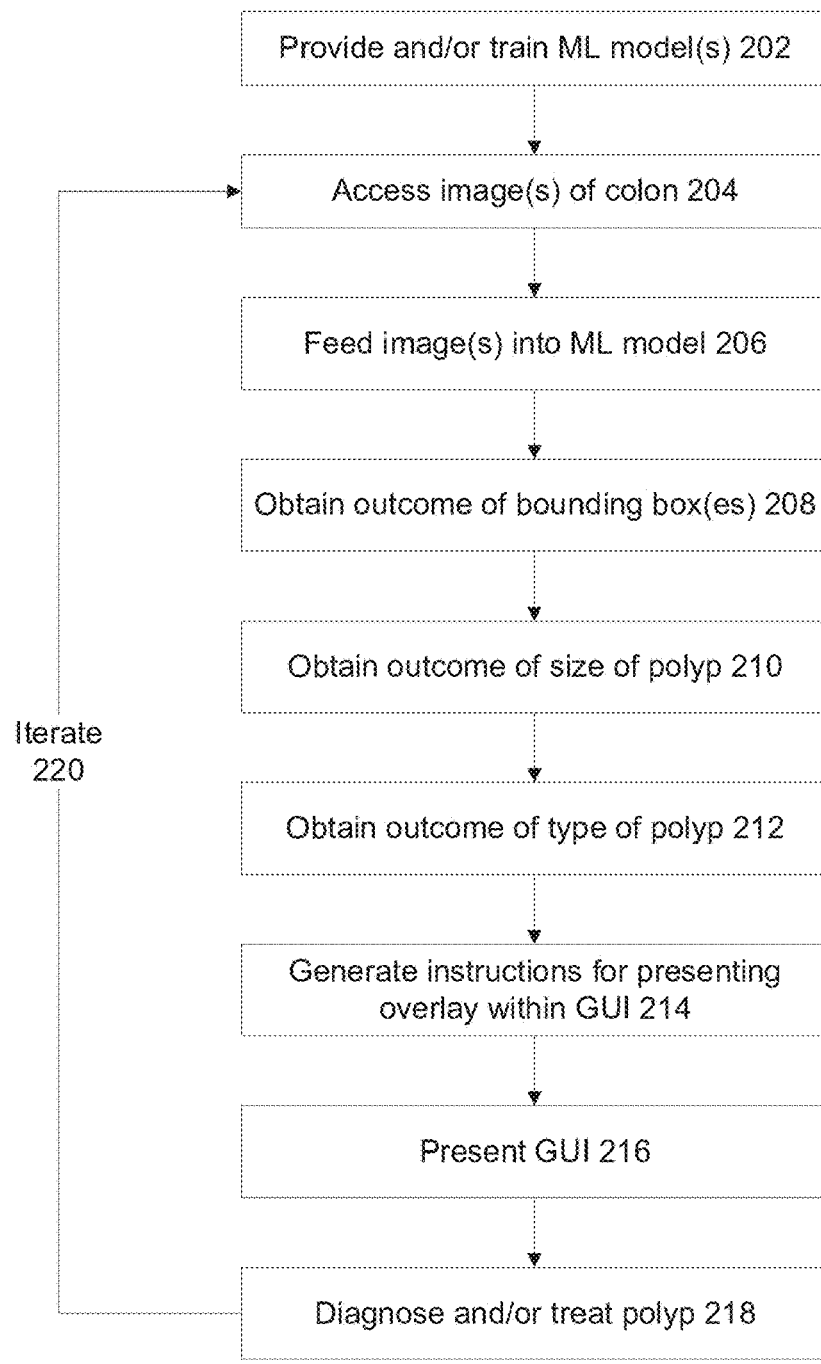
FIG. 2 is a flowchart of method of generating instructions for presenting a graphical user interface (GUI) for dynamically evaluating one or more polyps in endoscopic images of a colon of a subject using a trained ML model, in accordance with some embodiments of the present invention.
Figure 3:
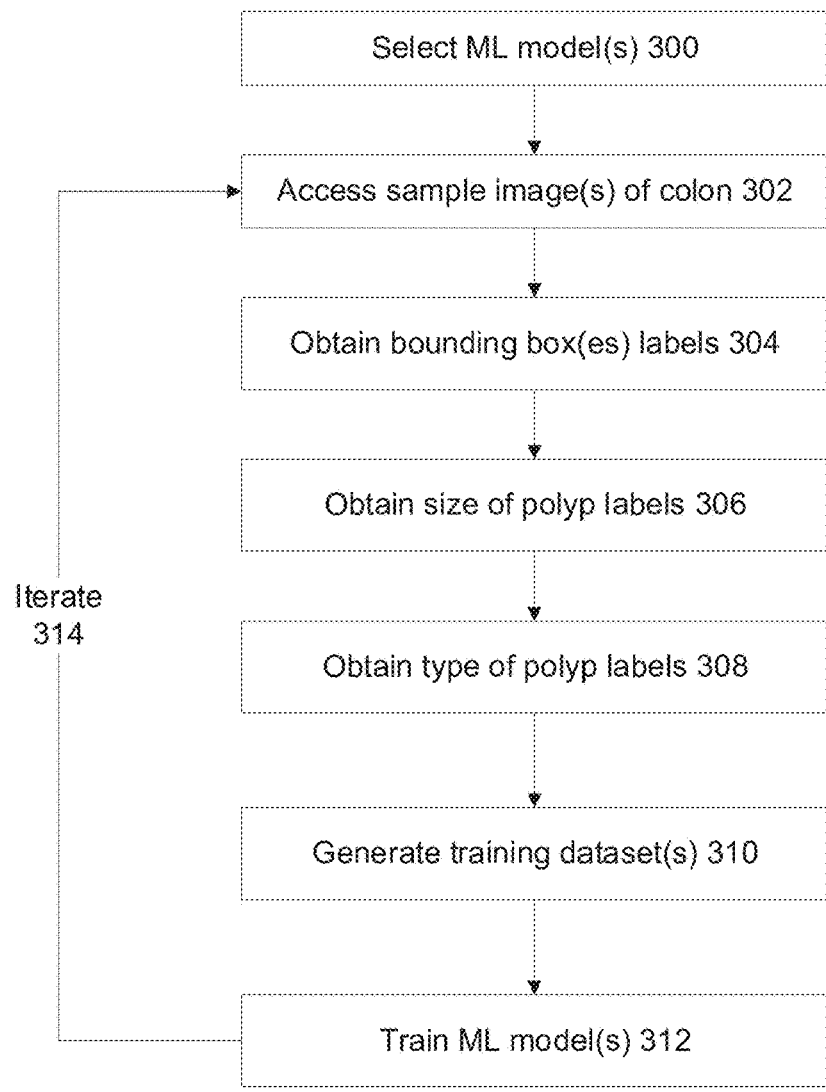
FIG. 3 is a flowchart of method of training a machine learning model for polyp detection, in accordance with some embodiments of the present invention.
Figure 4:
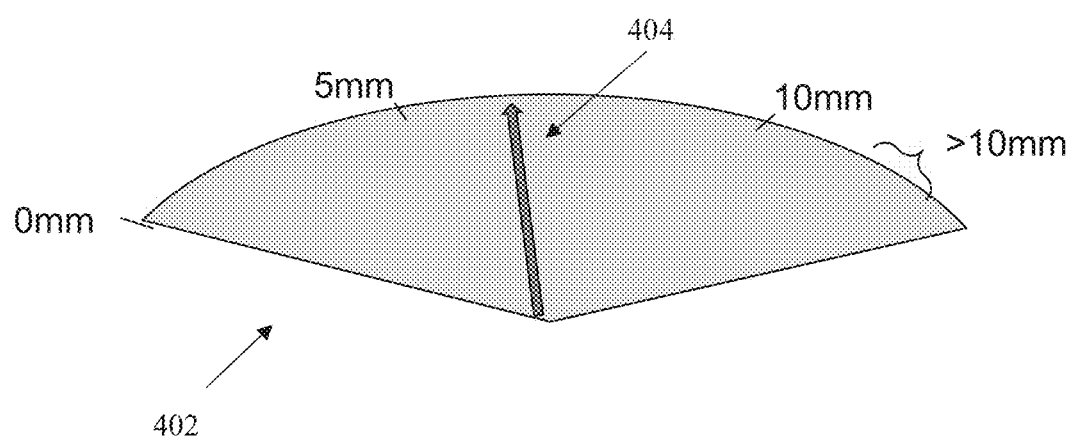
FIG. 4 is a schematic of a presentation of a size range of the polyp, in accordance with some embodiments of the present invention.
Figure 5:
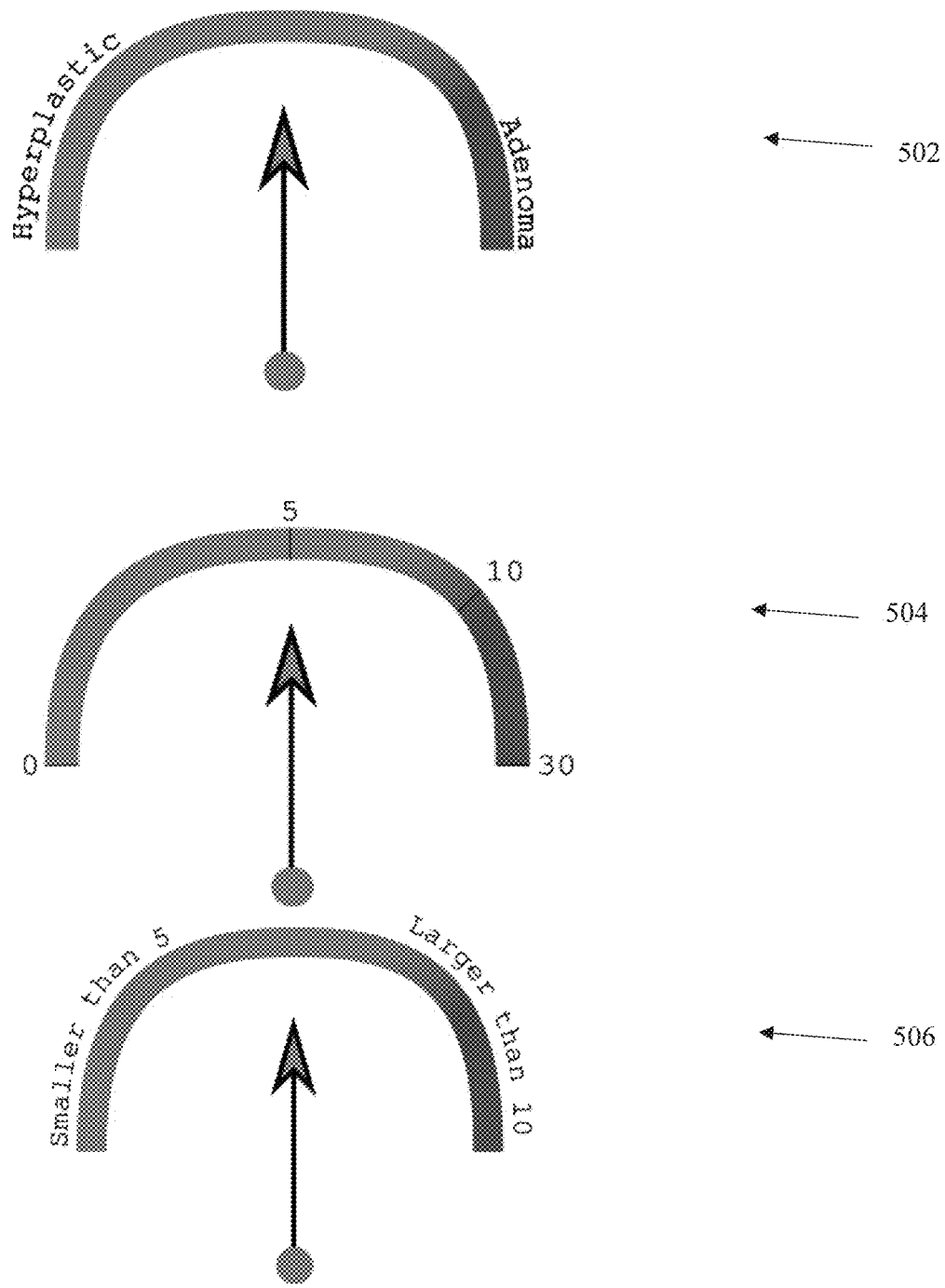
FIG. 5 includes schematics of presentations for depicting a size and/or type of the polyp, in accordance with some embodiments of the present invention.
Figure 6:
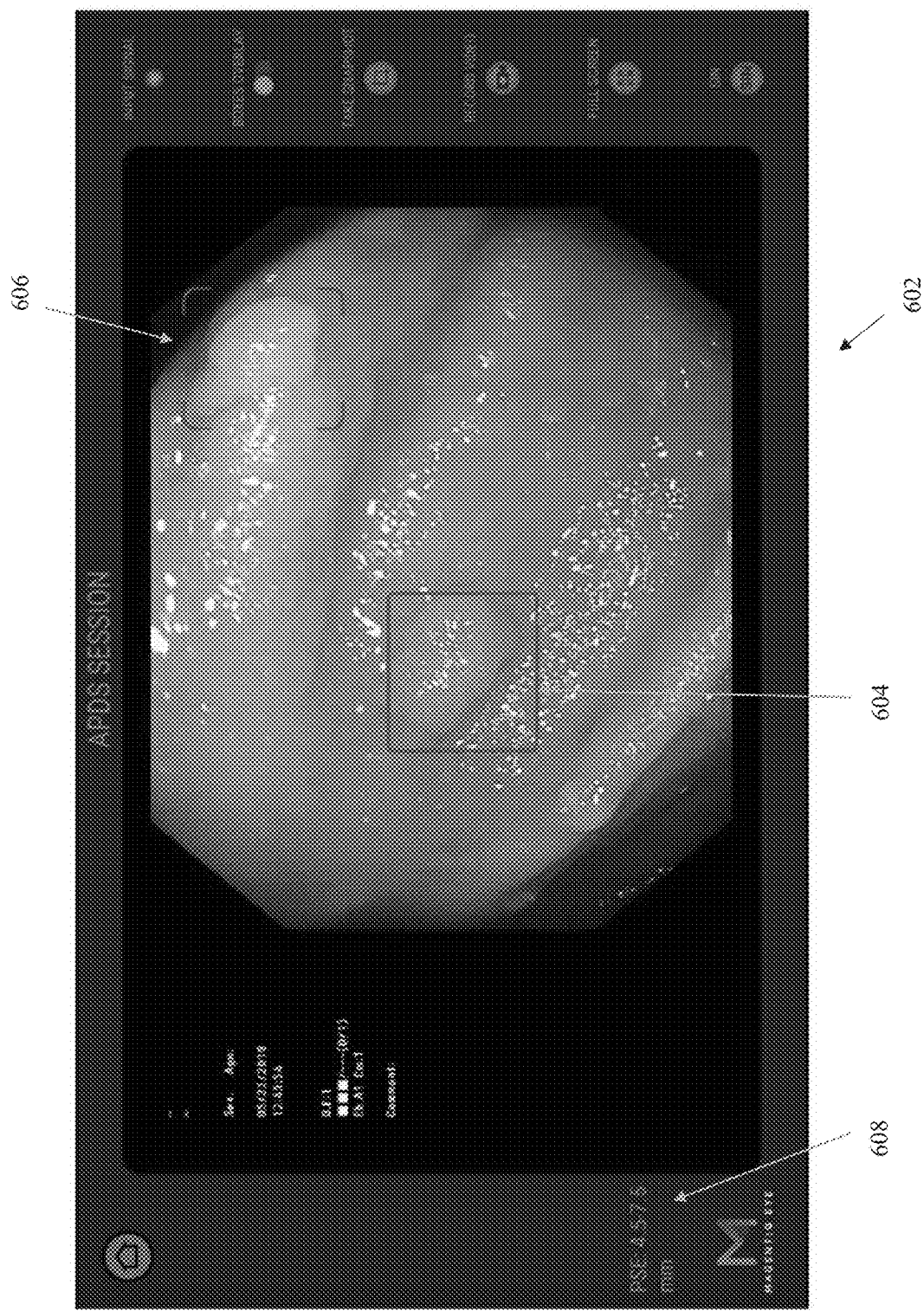
FIG. 6 is a schematic of an exemplary GUI depicting an overlay of an image of an internal surface of a colon, in accordance with some embodiments of the present invention.
Figure 7:
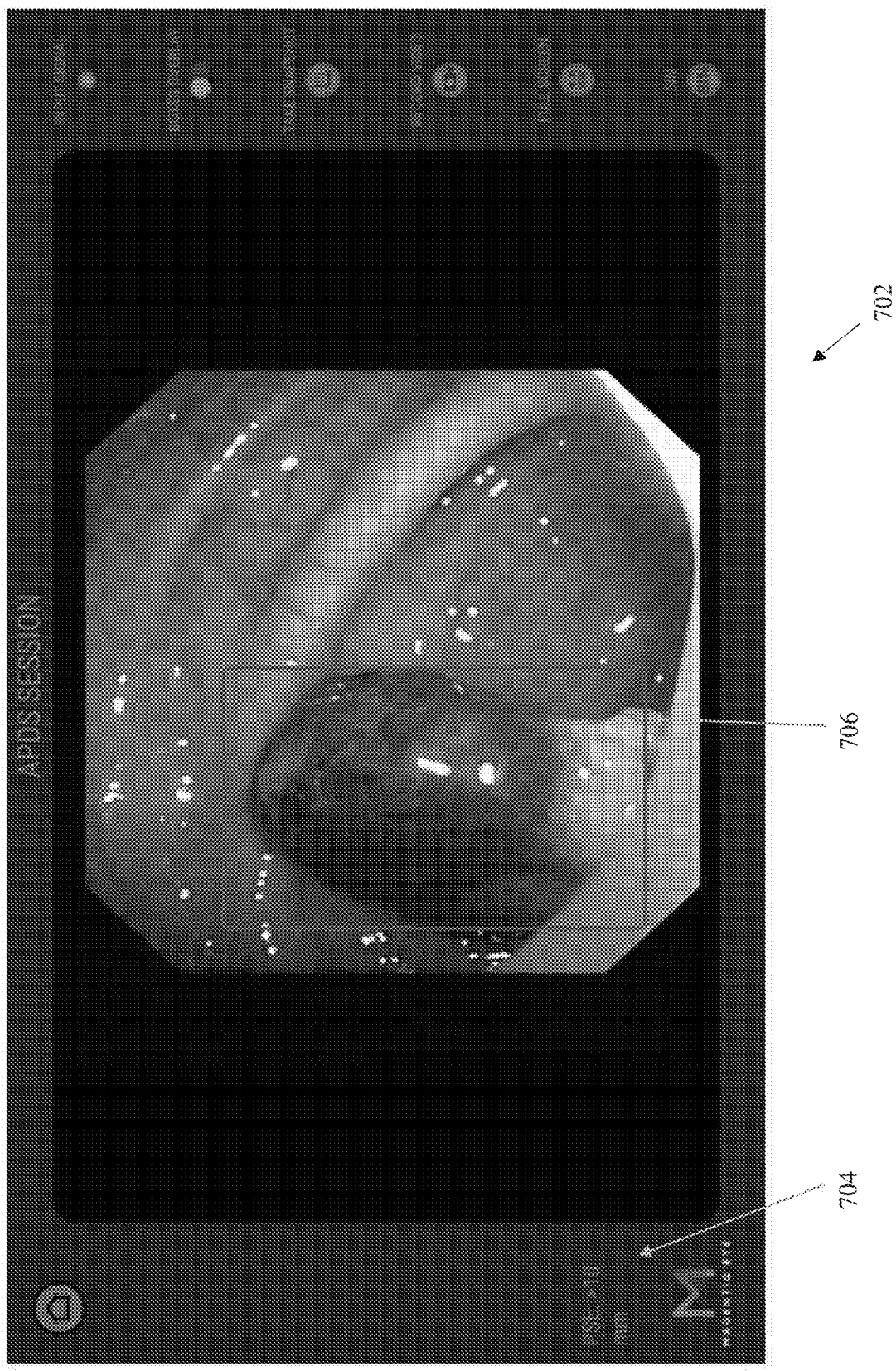
FIG. 7 is a schematic of an exemplary GUI presenting an open ended range for a large polyp identified in a bounding box of an image of an internal surface of a colon, in accordance with some embodiments of the present invention.
Figure 8:
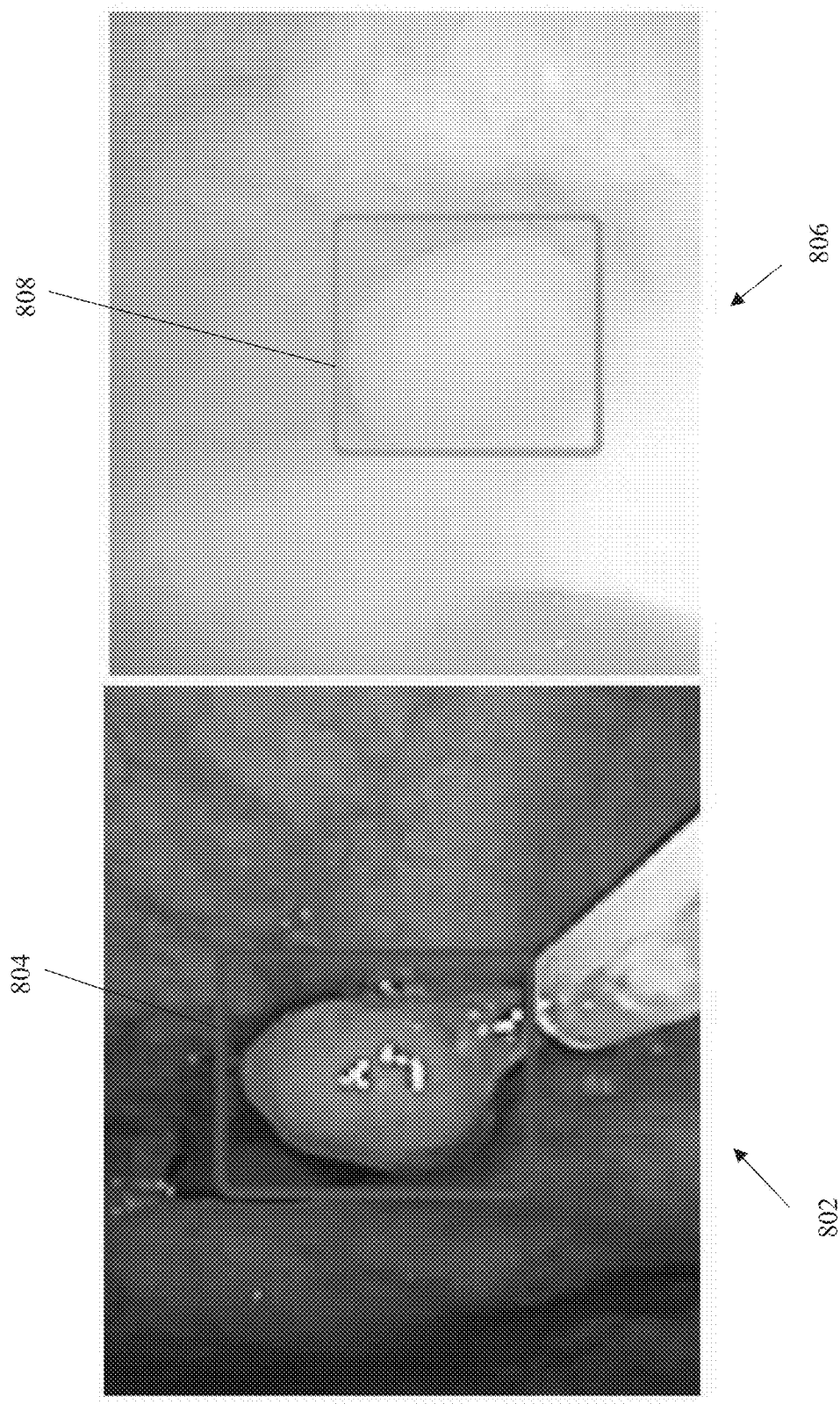
FIG. 8 is a schematic depicting an image with a bounding box of the first color (e.g., red) indicating adenoma, and another image with a bounding box of the second color (e.g., blue) indicating non-adenoma type, in accordance with some embodiments of the present invention.
Figure 9:
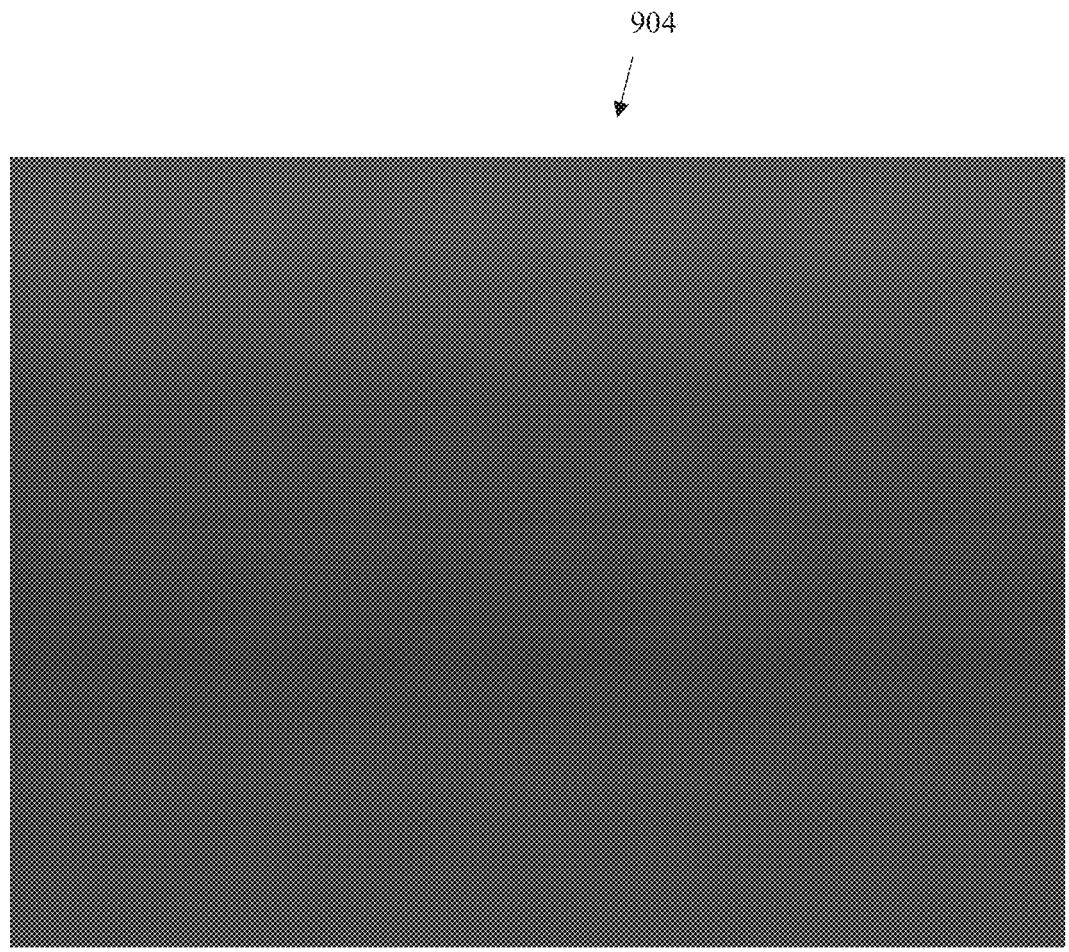
FIG. 9 is a schematic depicting a gradient palette from a first color indicating a low probability of the type being adenoma to a second color indicating high probability of the type being adenoma, in accordance with some embodiments of the present invention.
Figure 10:
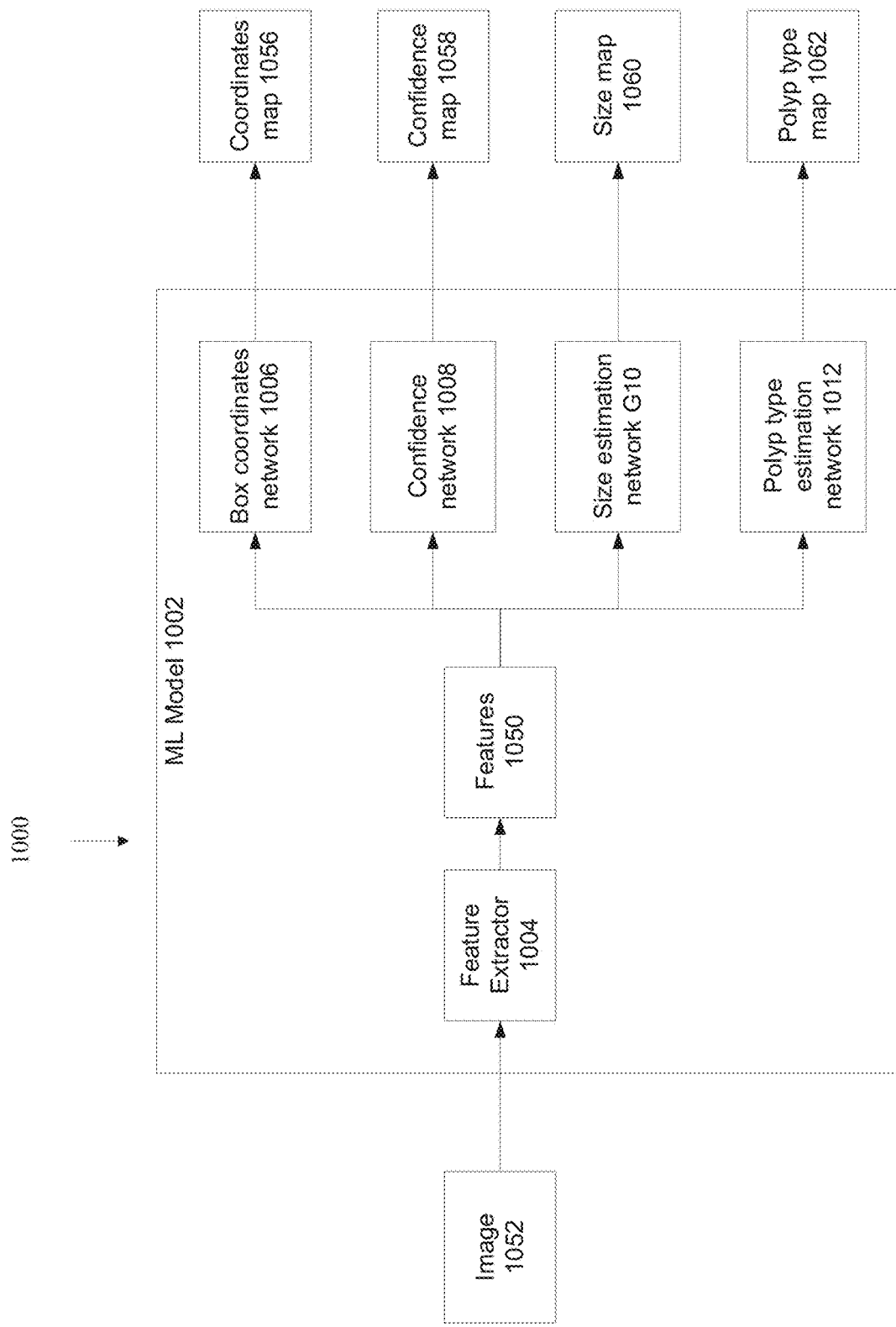
FIG. 10 is a schematic of an exemplary architecture of an ML model that generates an outcome of a size of a polyp and/or type of polyp, optionally a bounding box for the polyp, in response to an input of an image, in accordance with some embodiments of the present invention.

Reference is now made to FIG. 1, which is a block diagram of components of a system 100 for training a machine learning model and/or for using the trained machine learning model for estimating size and/or type of polyps depicted in images acquired by a camera located on an endoscope within a colon of a target patient, in accordance with some embodiments of the present invention. Reference is also made to FIG. 2, which is a flowchart of method of generating instructions for presenting a graphical user interface (GUI) for dynamically evaluating one or more polyps in endoscopic images of a colon of a subject using a trained ML model, in accordance with some embodiments of the present invention. Reference is also made to FIG. 3, which is a flowchart of method of training a machine learning model for polyp detection, in accordance with some embodiments of the present invention. Reference is also made to FIG. 4, which is a schematic of a presentation of a size range 402 of the polyp, in accordance with some embodiments of the present invention. Reference is also made to FIG. 5, which includes schematics 502-6 of presentations for depicting a size and/or type of the polyp, in accordance with some embodiments of the present invention. Reference is also made to FIG. 6, which is a schematic of an exemplary GUI 602 depicting an overlay of an image of an internal surface of a colon, in accordance with some embodiments of the present invention. Reference is also made to FIG. 7, which is a schematic of an exemplary GUI 702 presenting an open ended range 704 for a large polyp identified in a bounding box 706 of an image of an internal surface of a colon, in accordance with some embodiments of the present invention. Reference is also made to FIG. 8, which is a schematic depicting an image 802 with a bounding box 804 of the first color (e.g., red) indicating adenoma, and another image 806 with a bounding box 808 of the second color (e.g., blue) indicating non-adenoma type, in accordance with some embodiments of the present invention. Reference is now also to FIG. 9, which is a schematic depicting a gradient palette from a first color 902 indicating a low probability of the type being adenoma to a second color 904 indicating high probability of the type being adenoma, in accordance with some embodiments of the present invention. Reference is also made to FIG. 10, which is a schematic of an exemplary architecture 1000 of an ML model 1002 that generates an outcome of a size of a polyp and/or type of polyp, optionally a bounding box for the polyp, in response to an input of an image, in accordance with some embodiments of the present invention.

System 100 may implement the acts of the method described with reference to FIG. 2-10 optionally by a hardware processor(s) 102 of a computing device 104 executing code instructions stored in a memory 106. System 100 may perform one or more of: detection of polyp(s), estimation of a size of polyp(s) and/or estimation of a type of polyp(s) depicted in images captured by an imaging probe 112.

Imaging probe 112, for example, a camera located on a colonoscope, captures images within a colon of a patient, for example, obtained during a colonoscopy procedure. The colon images are optionally 2D images, optionally color images. The colon images may be obtained as a streamed video, and/or sequence of still images. Captured images may be processes in real time, and/or processed offline (e.g., after the procedure is completed).

Captured images may be stored an image repository 114, optionally implemented as an image server, for example, a Picture Archiving and Communication System (PACS) server, and/or an electronic health record (EHR) server. Image repository may be in communication with a network 110.

A computing device 104 receives the captured images, for example, directly in real time from imaging probe 112, and/or from image repository 114 (e.g., in real time, or off-line). Real time images may be received during the colonoscopy procedure, for presenting real time information regarding polyp to the operator, as described herein. The captured images may be received by computing device 104 via one or more imaging interfaces 120, for example, a wire connection (e.g., physical port, for example, output from imaging probe 112 is plugged into the imaging interface via a connecting wire), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Computing device 104 analyzes the captured image as described herein, and generates instructions for dynamically adjusting a graphical user interface presented on a user interface (e.g., display) 126, for example, elements of the GUI are injected as an overlay over the captured images and presented on the display, as described herein.

Computing device 104 may be implemented as, for example, a dedicate device, a client terminal, a server, a virtual server, a colonoscopy workstation, a gastroenterology workstation, a virtual machine, a computing cloud, a mobile device, a desktop computer, a thin client, a Smartphone, a Tablet computer, a laptop computer, a wearable computer, glasses computer, and a watch computer. Computing 104 may include an advanced visualization workstation that sometimes is add-on to a gastroenterology and/or colonoscopy workstation and/or other devices for enabling the operator to view the GUI created from a processing of the colonoscopy images, for example, real time presentation of estimated sizes of polyps depicted in the images and/or real time presentation of classification category indication type of polyp (e.g., adenoma, non-adenoma) depicted in the images, as described herein.

Computing device 104 may include locally stored software that performs one or more of the acts described with reference to FIGS. 2-10 and/or may act as one or more servers (e.g., network server, web server, a computing cloud, virtual server) that provides services (e.g., one or more of the acts described with reference to FIGS. 2-10) to one or more client terminals 108 (e.g., client terminal used by a user to view colonoscopy images, for example, a colonoscopy workstation that includes a display presenting the images captured by the colonoscope 112, a remotely located colonoscopy workstation, PACS server, remote EHR server, remotely located display for remote viewing of the procedure such as by medical students). Services may be provided over network 110, for example, providing software as a service (SaaS) to the client terminal(s) 108, providing an application for local download to the client terminals) 108, as an add-on to a web browser and/or a colonoscopy application, and/or providing functions using a remote access session to the client terminals 108, such as through a web browser, application programming interface (API), and/or software development kit (SDK), for example, for injection of GUI elements into colonoscopy images, and/or presenting the colonoscopy images within the GUI.

Different architectures of system 100 may be implemented. For example:

Computing device 104 is connected to multiple local devices 150, for example, over a network 110 and/or via imaging interface 120. Each local device 150 is connected to a respective imaging probe 112, for example, a colonoscope. Each local device 150 may be implemented, for example, as a standalone box, a mobile device, a standalone computer running code, and/or a local station running code. Each local device 150 may be sized to be small, for example, able to be placed on a palm of a hand, for example, having dimensions of about 3-15 centimeters (cm), or about 5-12 cm, or other values. Optionally, a respective local device 150 is installed in each respective procedure room. Local device 150 includes a first interface for connecting to imaging provide 112 and/or a second interface for connecting to network 110 and/or imaging interface 120. Exemplary data flow is now described. Local device 150 receives video and/or images captured by imaging provide 112 (e.g., via the first interface). The video and/or images are provided (e.g., transmitted, forwarded) to computing device 104 (e.g., via the second interface). Computing device 104, optionally implemented as a server, provides centralized services to multiple local devices 150. For example, a respective computing device 104 is installed per medical center, where the respective computing device 104 is connected to multiple local devices 150 installed in the procedure rooms of the medical center.

Computing device 104 processes the video and/or images as described herein, for obtaining one or more outcomes, for example, detection of polyp(s), estimation of a size of polyp(s) and/or estimation of a type of polyp(s), in the received image(s), and/or generation of overlays for the image indicating the detection, size, and/or type. The outcomes are provided for presentation on respective displays associated with respective imaging probe(s) 112 (e.g., via imaging interface 120 and/or network 110), for example, directly to the displays and/or to client terminals 108 associated with the displays, and/or to respective local devices 150 which may be connected to respective displays and/or client terminals 108 (e.g., via a third interface of local device 150 and/or via the second interface of local device 150). The architecture using local respective devices 150 connected to a central computing device 104 (e.g., server) is designed to guarantee robustness and/or no delay (e.g., no delay that the user is capable of visually detecting, and/or no significant delay). The robustness and/or no delay may be obtained by the localized installation, using localized and/or private networks, and/or relatively short distances. The robustness and/or no delay may be in contrast, for example, with an architecture that is cloud based, where the videos and/or images captured by multiple imaging probes are connected to the cloud, which is prone to interruptions, errors, and/or long delays. Moreover, installing the local device 150 which may be small, in contrast to installing a much larger device, saves space in the procedure rooms. The architecture enables quick deployment and/or scales easily, by the easy installation design of each local device 150 to additional imaging probes 112. It is noted that the training of the ML model(s) 122A may be performed, for example, centrally on another computing device. Copies of the trained ML model(s) 122A may be distributed to different computing devices 104 (e.g., servers) for inference of images obtained by respective connected devices 150. Alternatively or additionally, ML model(s) 122A may be trained on respective computing devices 104 (e.g., servers), for example, to generate respective customized ML model(s) 122A, such as for different medical institutions and/or different healthcare providers, and/or different medical sub-specialties and/or different sub-groups of patients (e.g., general screening versus screening in patients at high risk and/or screening in patients with genetic abnormalities). *Computing device 104 is connected between imaging probe 112 and display 126, for example, components of a colonoscopy workstation. Such implementation may be used for real time processing of the images captured by the colonoscope during the colonoscopy procedure, and real time presentation of the GUI described herein on display 126, for example, injecting the GUI elements and/or presenting the images within the GUI, for example, real time presentation of estimated sizes of polyps depicted in the images and/or real time presentation of classification category indication type of polyp (e.g., adenoma, non-adenoma) depicted in the images, as described herein. In such implementation, computing device 104 may be installed for each colonoscopy workstation (e.g., includes imaging probe 112 and/or display 126). Images received from the imaging probe 112 is fed into a locally stored copy of machine learning model(s) 112A for local inference. The outcomes may then be locally presented on a connected display.

Computing device 104 acts as a central server, providing services to multiple colonoscopy workstation such as client terminals 108 (e.g., includes imaging probe 112 and/or display 126) over network 110. In such implementation, a single computing device 104 may be installed to provide services to multiple colonoscopy workstations. Images received from imaging probes of different client terminals are centrally fed into trained machine learning model(s) 122A for centralized inference. The outcomes may then be provided back to respective client terminals, for example, for presentation on respective displays.

Computing device 104 is installed as code on an existing device such as server 118 (e.g., PACS server, EHR server) to provide local off-line processing for the respective device, for example, off-line analysis of colonoscopy videos captured by different operators and stored in the PACS and/or EHR server. Computing device 104 may be installed on an external device in communication over network 110 with server(s) 118 (e.g., PACS server, EHR server) to provide local off-line processing for multiple devices.

It is noted that machine learning model(s) 122A may be trained by computing device 104 using training dataset(s) 122B. Computing device 104 may use trained machine learning model(s) 122A for inference. In another implementation, machine learning model(s) 122A are trained on another device using training dataset(s) 122B. The trained machine learning model(s) 122A may be provided to computing device 104 for inference.

Client terminal(s) 108 may be implemented as, for example, as a colonoscopy workstation that may include imaging probe 112 and display 126, a desktop computer (e.g., running a viewer application for viewing colonoscopy images), a mobile device (e.g., laptop, smartphone, glasses, wearable device), and remote station server for remote viewing of colonoscopy images.

Hardware processor(s) 102 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include one or more processors (homogenous or heterogeneous), which may be arranged for parallel processing, as clusters and/or as one or more multi core processing units.

Memory 106 (also referred to herein as a program store, and/or data storage device) stores code instruction for execution by hardware processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 106 may store code 106A and/or training code 106B that implement one or more acts and/or features of the method described with reference to FIGS. 2-10, and/or GUI code 106C that generates the instructions for presentation within the GUI and/or that presents the GUI described herein based on the instructions (e.g., injection of GUI elements into the colonoscopy images, an overlay of GUI elements on the images, presentation of the colonoscopy images within the GUI, presentation of estimated sizes of polyps depicted in the images and/or presentation of classification category indication type of polyp (e.g., adenoma, non-adenoma) depicted in the images).

Computing device 104 may include a data storage device 122 for storing data, for example, machine learning model(s) 122A as described herein, training dataset(s) 122B for training the machine learning models) 122A, and/or image repository 114. Data storage device 122 may be implemented as, for example, a memory, a local hard-drive, a removable storage device, an optical disk, a storage device, and/or as a remote server and/or computing cloud (e.g., accessed over network 110).

Computing device 104 may include data interface 124, optionally a network interface, for connecting to network 110, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 104 may access one or more remote servers 118 using network 110, for example, to download updated imaging processing code, updated GUI code, and/or to obtain image for off-line processing.

It is noted that imaging interface 120 and data interface 124 may be implemented as a single interface (e.g., network interface, single software interface), and/or as two independent interfaces such as software interfaces (e.g., as APIs, network ports) and/or hardware interfaces (e.g., two network interfaces), and/or combination (e.g., single network interface, and two software interfaces, two virtual interfaces on a common physical interface, virtual networks on a common network port). The term/component imaging interface 120 may sometimes be interchanged with the term data interface 124.

Computing device 104 may communicate using network 110 (or another communication channel, such as through a direct link (e.g., cable, wireless) and/or indirect link (e.g., via an intermediary computing device such as a server, and/or via a storage device) with one or more of; server(s) 118, imaging probe 112, image repository 114, and/or client terminal(s) 108, for example, according to different architectural implementations described herein.

Imaging probe 112 and/or computing device 104 and/or client terminal(s) 108 and/or server(s) 118 include or are in communication with a user interface 126 that includes a mechanism designed for a user to enter data (e.g., mark a polyp for removal) and/or view the GUI including the colonoscopy images, estimated polyp size, and/or predicted polyp classification category. Exemplary user interfaces 126 include, for example, one or more of, a touchscreen, a display, a keyboard, a mouse, augmented reality glasses, and voice activated software using speakers and microphone.

Referring now back to FIG. 2, at 202, one or more machine learning models are provided and/or trained.

Optionally, a single ML model, that outputs both an indication of polyp size and an indication of polyp type in response to an input image depicting a polyp is provided and/or trained. The single ML model increases computational efficiency of a computing device running the single ML model, for example, in terms of reduced time to obtain the outcomes and/or reduced processing resource requirements and/or reduced memory requirements. The increased computational efficiency is in contrast to another implementation in which two ML models are trained and/or provided, where a first ML model generates an outcome of the size of the polyp and a second ML model generates an outcome of the type of the polyp. In some implementation, two ML models may be used, where a first ML model generates an outcome of the size of the polyp and a second ML model generates an outcome of the type of the polyp. As described herein, some features may be implemented to increase computational efficiency of a computing device executing the two ML models.

The machine learning model is trained on a training dataset of multiple records. Each record includes 2D images of the internal surface of the colon of the respective subject labelled with ground truth labels of respective bounding boxes enclosing respective polyps and an indication of size and/or a type of the respective polyp (e.g., indicating likelihood of developing malignancy). When a single ML model is used, each record may include ground truth labels of both the size and the type of the polyp. When two ML models are used, each ML model may be trained on a different training dataset, that may share the same 2D images and bounding boxes ground truth labels. One training dataset for training a first ML model further includes the ground truth label of size, and another training dataset for training a second ML model further includes the ground truth label of type.

At 204, one or more 2D images of an internal surface of a colon captured by an endoscopic camera located within a lumen of the colon, are accessed, for example, obtained in real-time by the camera, and/or obtained from a storage device such as a server, computing cloud, PACS server, hard disk drive, memory, and the like.

Optionally, the 2D image excludes a depiction of an external measurement tool. Such external measurement tools are used in some standard approaches to help estimate the size of polyps, for example, a ruler and/or element with known size. Measurement of polyp size is done without necessarily using such external measurement tools, using at least some implementations of the ML model, as described herein.

The image is a 2D image, optionally in color. The image depicts the inside of the colon, and may or may not depict a polyp.

Images may be captured as a video stream, Individual frames of the video stream may be analyzed.

Images may be analyzed individual, and/or as a set of sequential images, as described herein. Each image in the sequence may be analyzed, or some intermediate images may be ignored, optionally a predefined number, for example, every third image is analyzed, with the intermediate two images being ignored.

The images are captured when the endoscope is located inside the colon and/or moved within the colon of the patient. For example, the endoscope is advanced forward (i.e., from rectum to cecum), retraced (e.g., from cecum to rectum), and/or the orientation of at least the camera of the endoscope is adjusted (e.g., up, down, left, right), and/or the endoscope is left in place.

At 206, the 2D image is fed into the machine learning model. The 2D image may be fed into the single ML model, or into both ML models.

At 208, an outcome of a bounding box(es) that depicts a polyp therein is obtained from the machine learning model. In the case of two ML models, two bounding boxes may be obtained, one for each ML model. Features to increase computational efficiency of the computing device running the two ML models may be implemented, for example, as described herein.

Optionally, the ML model is set to generate a single bounding box per polyp. When two or more polyps are depicted in the 2D image, two or more bounding boxes may be generated, i.e., one box per polyp.

At 210, an indication of size of the polyp is obtained as an outcome of the ML model.

Optionally, the value obtained from the ML model is a logarithm of the size. In such implementation, the logarithm of the size is converted to a standard numerical value of the size, by using a set exponentiation base raise to the power of the logarithm of the size, as described herein.

Optionally, when the indication of the size of the polyp is a scalar value, the scalar value may be converted to a range computed to cover a selected percentage of ground truth sizes in the training dataset. The range may be a half-open range, such as when insufficient ground truth is available in the training dataset to obtain an accurate estimation above a threshold.

Exemplary processes for generating the range of the size of the polyp are now described.

In a first exemplary approach, for the scalar size estimation, a range wide enough to cover about 85% (or about 80%, or about 90%, or other values) of sample values from the training dataset where the ML model gave such scalar value, is generated. For example, when the ML model estimate is a size value of an interval from 4 to 5 millimeter (mm), the training dataset is searched to find examples (e.g., all examples) where the ML model generated the estimation from that interval/Ground truth size values (e.g., all values) for these examples are obtained. A range that include 85% (or other values) of these values is found. This process may be performed in advance, for generate mapping, for example, 3..4=>0..4; 4..5=>2..6; 5..6=>4-7, and the like. This mapping is used during runtime (i.e., inference) to convert the scalar size into a range. For example, when the model estimates the size as 4.85 mm, according to the example mapping the range is provide as being from 2 to 6 mm. Conceptually, when the ML model determines that the size is "4.85 mm", the process to covert to range indicates "with probability of 85% the true size is between 2 and 6 mm".

A second exemplary approach is now presented. The second approach may be simpler, less "smart", less comprehensive, and/or more reliable. Fixed ranges may be defined, optionally three ranges, for example, <5 mm, 5-100 mm and >10 mm. In another example, <3 mm, 3-10 mm, and >10 mm. Ranges may be selected based on clinical significance, for example, small polyps <5 mm may remain or be easily removed using a first tool. Medium sized polyps of 5-10 mm may be removed using standard approaches. Large polyps >10 mm may require special attention, for example, surgical consultation to evaluate surgical removal. Moreover, there may be insufficient ground truth available to provide an accurate estimation at the lower and/or upper limits of the range, since such small and/or large polyps are not frequently encountered. Two thresholds may be defined for size estimation by the model, denoted X and Y (X<Y). When the ML model generates the size estimation below X, the process returns the range <5 mm. When the ML model size estimation is between X and Y, the process returns the range 5-10 mm. When the ML model size estimation is above Y, the process returns the range >10 mm. The thresholds X and Y are chosen in advance for a concrete ML model such that the mapping according to these thresholds gives the best performance over the training dataset. Threshold Y may be chosen such that it gives the best F1 score for classifying polyps between ranges <10 mm and >10 mm. Threshold X may be chosen such that it gives the best F1 score for classifying polyps between range <5 mm and >5 mm, among the polyps where the model estimation is below Y.

The first approach may be theoretically better, as it is able to give a more specific range than the second approach. However, the mapping generated by the first approach may in some cases maps to too wide ranges, which is not clinically practical for the user performing the colonoscopy (e.g., gastroenterology, other doctor). The second process may be used until enough data is available for higher accuracy and narrower, more clinically significant ranges.

A third exemplary approach is now presented. In terms of mathematical representation, the range is defined as follows: lowBoundary:=A·size+B, and high Boundary:=C·size+D, where size denotes the polyp size predicted by the ML model, low and high boundaries denote the size range that is provided for presentation on the screen, and parameters A, B, C and D are coefficients.

A fourth exemplary approach is now presented.

At 212, the type of the polyp is obtained as an outcome of the ML model. The type may be a classification category, for example, adenoma, non-adenoma, and/or unknown, as described herein.

At 214, instructions are generated for presenting within the GUI, an overlay of the bounding box over the polyp and the indication of size and/or type of the polyp.

Reference is now made back to FIG. 4. Size range 402 may be presented as an overlay of the 2D image, within the GUI, optionally external to borders of the 2D image. Size range 402 may be presented as a numeric interval: MIN-MAX mm (ex. 5-7 mm), for half open ranges->MIN mm (ex. >10 mm) or <MAX mm (ex. <4 mm). Size range 402 may be presented, for example, similar to a car speedometer, using an arrow 404 to indicate the estimated size within a range where major values (e.g., 0, 5 mm, 10 mm, and greater than 10 mm) are indicated.

Reference is now made back to FIG. 5. Schematics 502-6 depict a gauge and/or compass with indications, for example, colors, to indicate size and/or type.

Schematic 502 depicts a type of the polyp. By default the arrow in the gauge points to the top middle location (North). This location indicates that the ML model is unable to accurately classify the polyp (e.g., does not enough data to detect the type of the polyp, and/or probability that the polyp is of a certain type and/or accuracy of detection is below a threshold). The left point of the gauge (West) depicts a first pattern (e.g., first color) indicating that the ML model detected a first type for the polyp, for example, hyperplastic polyp. The right side of the gauge (East) depicts a second pattern (e.g., first second) indicating that the ML model detected a second type for the polyp, for example, an adenoma. The arrow is moved either right or left according to the detected polyp type. The degree by which the arrow is rotated indicates the confidence of the ML model, the greater the absolute value of the degree the higher is the confidence.

Schematic 504 depicts an example for presenting a size of the polyp. The markers on the gauge indicate the estimated polyp size.

Schematic 506 depicts another example for presenting a size of the polyp. As shown, the leftmost point of the gauge indicates high confidence of a polyp with size smaller than 5 mm and the rightmost point on the gauge indicates high confidence of a polyp with a size larger than 10 mm. The degree by which the arrow is rotated indicates the confidence of the ML model, the greater the absolute value of the degree the higher is the confidence.

Referring now back to 214 of FIG. 2, optionally, the instructions are for presenting the indication of size and/or type external to borders of the 2D image.

Optionally, the instruction are for presenting the indication of size and/or type for a single bounding box closest to a center of the single 2D image when two or more different bounding boxes are generated for a single 2D image. Optionally, no indication of size and/or type is presented for other boxes located further away from the center than the single bounding box.

Reference is now made back to FIG. 6. A bounding box 604 of a polyp closest to a center of the image is shown as a full solid bounding box. Another bounding box 606 of another polyp further away from the center is marked differently, for example, by marking the corners of the box, rather than a full border. The estimated size and/or type 608 are presented outside of the borders of the image. Size is presented as a range, as described herein. Size and/or type 608 is presented for a single polyp at a time, currently for the polyp in bounding box 604 which is closest to the center.

Reference is now made back to FIG. 7. An exemplary GUI 702 presenting open ended range 704 for the large polyp identified in bounding box 706 of the image of the internal surface of a colon is depicted. The estimated size 704 is presented outside of the borders of the image.

Referring now back to 214 of FIG. 2, optionally, the instructions are for presenting the bounding box with a color and/or border style by applying a set of rules to the indication of size and/or type. Changing the color and/or border style of the bounding box presents the size and/or type of the polyp to the user without adding additional overlays such as text and/or other markings, which may distract the user performing the colonoscopy. For example, the bounding box with a first color when the type is adenoma, a second color when the type is non-adenoma. In another example, a third color may be used when the type is unknown, such as when the probability of the inference is below a threshold. In another example, only the first color and third color are used.

Reference is now made back to FIG. 8. Image 802 with bounding box 804 of the first color (e.g., red) indicating adenoma, and another image 806 with bounding box 808 of the second color (e.g., blue) indicating non-adenoma type, is shown.

Referring now back to 214 of FIG. 2, alternatively or additionally, the bounding box is presented with a color hue according to estimated probability of the inference of the type of the polyp, optionally estimated probability that the type is an adenoma.

Reference is now made back to FIG. 9. A gradient palette from first color 902 indicating a low probability of the type being adenoma to second color 904 indicating high probability of the type being adenoma, is shown.

Referring now back to 214 of FIG. 2, optionally, instructions are generated for presenting within the GUI, an indication of what to do with the polyp. The indication of size and/or type of the polyp may be evaluated, for example, using a set of rules. The instructions for presentation within the GUI may be, for example, for at least one of: removal of the polyp, tool to use to remove the polyp, a suggested approach for removal of the polyp, and/or instructions for leaving the polyp in situ. The set of rules may be defined, for example, per medical institution, per user, and/or in general for different users.

Alternatively or additionally, instructions for treating the polyp are generated based on a treatment ML model. The overlay of the bounding box over the polyp and the indication of size and/or type of the polyp are fed into the treatment machine learning model. The treatment ML model generates an outcome indicating whether the polyp is to be removed or left in situ. The treatment machine learning model may be trained on a training dataset that includes multiple records. Each record includes a respective outcome of a sample bounding box over a sample polyp and the indication of size and/or type of the sample polyp obtained from the machine learning model in response to a sample 2D image(s), labelled with a ground truth indicating whether the sample polyp was removed or left in situ, Stacking approaches may be At 216, the GUI is presented on a display according to the generated instructions, for example, on a display of a colonoscopy workstation, a monitor in the operating room, a screen of a viewing room, a smartphone, and on a display of another terminal (e.g., administrative server, and/or terminal).

At 218, the polyp may be diagnosed and/or treated, manually by a user and/or automatically by a robot. The diagnosis and/or treatment may be according to the generated recommendations, as described herein.

Optionally, the polyp is excised when the indication of size and/or type of the polyp meets a set of rules, as described herein.

The size and/or type of the polyp may be stored, for example, in an electronic health record (EHR) of the subject stored by an HER server. The size and/or type of the polyp may be printed on a sticker, which may be stuck to a container in which the excised polyp is placed, for example, when the polyp is being sent to pathological analysis.

At 220, one or more features described with reference to 204-218 may be iterated. Iterations may be performed for real time evaluation of 2D images during the colonoscopy procedure.

Additional features may be implemented during the iterations of one or more of 204-218, for example, debouncing and/or avoiding or reducing fluctuations of the detected polyp type for the same imaged polyp.

In some implementations, the ML model(s) does not store data between successive images (e.g., frames of a video), but rather, each frame is independently processed. Such independent processing of each frame may lead to inconsistencies in detected size and/or type for the same polyp, since the same polyp is depicted in different images and being evaluated anew each time for each image. For example, in some frames, viewed in a slightly different angle, the size and/or type may change due to the ML model making wrong identifications from the different angles, even when the size and/or type are correct for the majority of other frames. Approaches for providing a stable estimated size and/or estimated type by eliminating (and/or reducing) prediction bounces over time, are now described. None-stable estimated size and/or type may confuse the operator and/or be difficult to use clinically.

In another exemplary implementation, during iterations, in which multiple successive 2D images are fed into the machine learning model, multiple successive bounding boxes and respective indications of size and/or type are obtained. A sequence(s) of overlap between the bounding boxes is identified (e.g., IoU above a threshold). For each sequence of overlapping bounding boxes, indications of size and/or type over a selected time interval (e.g., about 1 second, or 2 seconds, or 3 seconds, or 1-3 seconds, or other values) are identified. Outlier indications are removed, for example, using a threshold to remove the highest and/or lowest predictions, for example, the highest 10% and/or lowest 10%. The remaining indications of size and/or type are averaged (i.e., each set of size, and each set of type) are averaged to obtain a single size and/or a single type. During subsequent iterations, additional scalar values for a next single size and/or type of subsequence images are collected. When the scalar value for the next single size and/or type is a higher than the computed single size and/or single type (e.g., computed by averaging) by a margin, the higher scalar value is selected as the outcome for presentation. The margin ignores small changes, which may be due to statistical fluctuations which are irrelevant. When the size changes over time for the same polyp, the higher predicted value is more likely to be the true value. Lower values may be a result of different viewing angles, different lighting, and/or other image anomalies. As such, higher values may be considered for size, with the size being adjusted to the new higher value. Smaller values for the size may be ignored, based on the assumption that the previous higher values are correct and the smaller value is an anomaly.

Alternatively or additionally, as described herein in additional herein, the obtained size which is an outcome of the ML model may be converted to a range and/or the computed single size (as described in the previous paragraph) may be converted to a range. The range of size may be provided rather than specific values, which stabilizes the prediction within the range, even when the specific predicted size varies within the range. In some implementations, a half-range may be presented when after debouncing the estimated size is at or above a threshold. For example, when the size after debouncing is 8.5 mm, and the threshold is 8.5 mm, the value is presented as >10 mm. This may be done in order to better balance precision and recall of binary classification between polyps "larger than 10 mm" and "smaller than 10 mm", i.e., it is desired to have the recall high, and precision as good as possible. The threshold used is an example, and may vary according to ML models and/or training data.

Optionally, to avoid or reducing fluctuations of the detected polyp type for the same imaged polyp in successive images, a minimum number of detections of a different polyp type are determined before the polyp type is changed. During the iterations, 2D images may be sequentially fed into the machine learning model to obtain respective bounding boxes and indications of size and/or type of the polyp. The size and/or type of the polyp is switched from a previous value to a new value when a number of consecutive bounding boxes above a predefined threshold are associated with the new value.

In an example implementation, bounding boxes generated by the ML model in response to an input of 2D images are assigned a unique box ID for every detected polyp. A data structure, for example a matrix, with predefined constants for every transition from every polyp type to every other polyp time is defined, for example, a 3×3 matrix for polyp types of adenoma, non-adenoma, and unknown. The matrix values equal the minimum number of subsequent detections of the same polyp type for a given unique box ID before the prediction presented to the user from the previous type of that box ID is switched to the new box ID. The initial type of every box ID is Unknown.

An evaluation may be made to determine if a detected bounding box in a certain image depicts the same polyp as in another box in one or more preceding images. A history of detected bounding boxes is kept, where the same box ID is assigned for all boxes which are recognized as belonging to the same polyp.

An exemplary approach is now described for tracking the detected polyps. 2D images are sequentially fed into the machine learning model to obtain respective bounding boxes and indication of size and/or type of the polyp. Records are generated for the 2D images, where each record for a respective 2D image includes coordinates of the respective bounding box, a unique box ID assigned for each box associated with each unique polyp, and a last seen parameter identifying a frame ID of a last 2D image (of the multiple 2D images) where the unique box ID last appeared. In response to a new unique box ID of a new box of a new 2D image, a search is performed for at least one record of a previous box that overlaps with the new box. The overlap may be detected by having an intersection over union (IoU) less than a threshold. The unique box ID of the new box is set to the value of the unique box ID of the previous box that overlaps with the new box. When no record is found in the search, a new value is assigned to the unique box ID of the new box. Records that have an overlapping box in the new 2D image are removed. New records are created for boxes of the new 2D image. Records for which the last seen parameter is smaller than the frame ID of the new 2D image by a predefined constant are removed.

Record(s) of the previous box that overlaps with the new box may found when the previous box overlaps with the new box by having an intersection over union (IoU) less than a threshold. Alternatively or additionally, Record(s) of the previous box that overlaps with the new box may found by tracking each box in the plurality of records and comparing new boxes against the tracked value of the boxes in he plurality of records. The tracked values may be computed by a tracking process (e.g., tracking ML model) that is fed an input of a current image, a bounding box of a polyp depicted in the current image, and a subsequent next image. The tracking process generates an outcome of an estimate of the bounding box for the polyp on the next frame. The tracking value indicates an adjustment of coordinates of the bounding box of a current frame for the next frame.

Optionally, when two ML models are used during the iterations, one ML model that generates the size of the polyp and another ML model that generates the type of the polyp, both ML models may be run in parallel in a GPU. The results may be combined on the GPU and then the combined results are copied to the CPU. This enables using both ML models together (which were trained separately) without necessarily increasing GPU-CPU communication time. An exemplary process is now described. The 2D image is fed into a first machine learning model that generates a first bounding box over the polyp and the indication of size. The 2D image is also fed into a second machine learning model that generates a second bounding box over the polyp and the indication of type. The first and second machine learning models are running on a first processor (e.g., GPU). The first process find overlapping first and second bounding boxes, for example, an overlap is found when an IoU of the first and second bounding boxes is below a threshold. One of the first and second bounding boxes that are overlapping is selected to create a final list of boxes. The list of boxes is provided a second processor (e.g., CPU). The list of boxes may be used for creation of a list of records of the boxes, for example, for tracking boxes to determine when the same polyp is in the boxes or a new polyp is in the boxes, as described herein.

Optionally, a dominant machine learning model and a non-dominant machine learning model from the first and second machine learning models. The dominant ML model may be selected when both the first and second ML models generate boundary box detection outcomes. Since only one boundary box is needed for the image, the dominant ML model is selected to provide the boundary box. The dominant machine learning model is run on the first processor (e.g., GPU) and the bounding box outcome of the dominant machine learning model is provided to the second processor (e.g., CPU). The dominant ML model uses the boundary box for other processing, such as for generation of the overlay of the image, as described herein. In parallel, the non-dominant machine learning model is run on the first processor (e.g., GPU) to find overlapping boxes of the non-dominant ML model (i.e., one of the first and second bounding boxes), which are passed to the second processor (e.g., CPU).

Referring now back to FIG. 3, at 300, one or more ML model architectures are selected for training.

A single ML model may be selected for generating outcomes of both size and type for a detected polyp, optionally in addition to a detected boundary box. Alternatively, two ML models may be selected, where a first ML model generates an outcome of size optionally in addition to a detected boundary box, and a second ML model generates an outcome of type optionally in addition to a detected boundary box.

Reference is now made back to FIG. 10. Exemplary architecture 1000 of ML model 1002 that generates the outcome of the size of the polyp and/or type of polyp, optionally the bounding box for the polyp, in response to an input of an image, is depicted.

Optionally, ML model 1002 is implemented as a neural network.

ML model 1002 includes a feature extractor component 1004, a box coordinate network component 1006, a confidence network component 1008, and a size estimation component 1010 and/or a polyp type estimation component 1012.

In the single implementation of the ML model that outputs both the size and type of the polyp, both size estimation component 1010 and/or polyp type estimation component 1012 are included. It is noted that architecture 1000 may be adapted to generate two ML models. In the first ML model that generates the size but not the type, size estimation component 1010 is included and polyp type estimation component 1012 is excluded. IN the second ML model that generates the type but not the size, size estimation component 1010 is excluded and polyp type estimation component 1012 is included.

Feature extractor component 1004 generates multiple features maps 1050 (e.g., output images) in response to an input of an image 1052. Features maps 1050 may be high dimensional vectors assigned to pixels (e.g., each pixel) of the input image 1052 (e.g., about 100 or 200 dimensions, or other values). The pixel dimensions may be the same for each image in the set, but their sizes may be different.

Each feature map 1050 is independently fed into each one of box coordinate network component 1006, confidence network component 1008, size estimation component 1010 and/or polyp type estimation component 1012.

Box coordinate network component 1006 generates coordinate maps 1056 indicating coordinates of candidate bounding boxes when applied to each respective feature map. For example, box coordinates network 1006 produces an image, each pixel of which is a 4-dimensional vector, representing the coordinates of candidate bounding boxes.

Confidence network component 1008 generates confidence maps 1058 indicating an estimated probability of a respective pixel being a detected polyp when applied respectively to each feature map. Confidence network 1008 produces an image of a 1-dimensional vector that represents the estimated probability that the corresponding pixel from the coordinates map is really a detected object.

Size estimation component 1010 generates size maps 1060 indicating an estimated polyp size when applied to each respective feature map. Each respective size map may include at least one 1-dimensional vector representing, whose 1 dimension represents the estimated polyp size, optionally a logarithm of the estimated size of the polyp. The logarithm of the estimated size is converted to the size using an exponentiation base that is an adjustable hyperparameter, as described herein. The exponentiation base is set to different values for different size maps computed from different feature maps. The smaller the feature map the larger the exponentiation base. This may be done since one pixel of a smaller feature map corresponds to a bigger region of the image, while the size network estimates normalized polyp sizes. This detail helps the network to better handle too big polyp sizes, but reducing the variance in ground truth map. In contrast, if just plain absolute sizes were used, then the network would be unable to generate large size values for large polyps, due to the training process. By using logarithms instead of sizes and using different exponentiation bases for feature maps of different resolutions, this technical problem of handling large polyps is addressed.

Polyp type estimation component 1012 generates polyp type maps 1062 indicating a polyp type when applied to each respective feature map.

The bounding box is obtained by stacking the coordinates maps, the confidence maps, the size maps, and the polyp type maps. Optionally, when the coordinates map is stacked on top of the confidences map, an image of 5-dimensional vectors that represent bounding boxes are obtained. One component of these vectors is the estimated probability the box to be really a box, and the rest four are box coordinates. Further stacking the size map on top of the box coordinate map and the confidence map generates 6-dimensional vectors that represent boxes, one dimension for probability, 4 dimensions for coordinates and the last dimension is for size.

When all pixels from all outputs of the box coordinates and confidence networks, produced from each feature map, are collected, a large amount of candidate bounding boxes are obtained. A filtering process is applied to filter out the vast majority of the bounding boxes and leaves only a few boxes that represent the network's response to the input image. Each remaining box, after filtering, is associated with a type and/or size value for the polyp depicted therein.

Size maps and/or polyp type maps may be 2D images, where each pixel of which is a size value and/or type value, denoting an estimation for a corresponding patch of the original input image 1052. Each size map and/or type map has lower resolution that the original input image 1052. One pixel of size map and/or type map corresponds to a patch (i.e., not to a single pixel) of the original input image 1052.

Optionally, the architecture of the ML model(s) 1002 is an adaptation of a baseline ML model designed to generate an outcome of only the boundary boxes, without size and/or type, for example, where feature extractor component 1004, box coordinate network component 1006, and confidence network component 1008 are based on RetinaNet (e.g., ResNet50-FPN feature extractor), which is adapted to further include size estimation component 1010 and/or polyp type estimation component 1012.

It is noted that ML model(s) 1002 is an exemplary implementation. Other ML model architectures may be implemented, for example, statistical classifiers and/or other statistical models, neural networks of various architectures (e.g., convolutional, fully connected, deep, encoder-decoder, recurrent, graph), support vector machines (SVM), logistic regression, k-nearest neighbor, decision trees, boosting, random forest, a regressor, and/or any other commercial or open source package allowing regression, classification, dimensional reduction, supervised, unsupervised, semi-supervised or reinforcement learning. Machine learning models may be trained using supervised approaches and/or unsupervised approaches.

Referring now back to FIG. 3, at 302, samples images of the colon are accessed. Each image is of a respective internal surface of a respective colon of a respective subject captured by an endoscopic camera located within a respective lumen of the respective colon. Samples images may be videos of multiple frames and/or individual images. Images may be of different subjects, for example, of different ages and/or different genders. Samples images include images that depict polyps of various sizes and/or types, and other images that do not depict any polyps.

At 304, bounding box ground truth labels for polyps depicted in the sample images are accessed. The bounding boxes may be created, for example, manually by users viewing the images, for example, using a GUI designed to mark bounding boxes.

At 306, sizes of polyps depicted in the sample images are obtained.

Sizes may be measured, for example, using standard manual approaches, for example, visual inspection by an expert, and/or measurement using an external measurement tool that is inserted into the colon via the colonoscope (e.g., ruler, presized loop, and the like).

Optionally, a logarithm of the size of the respective polyp is computed. The size included in the records of the training dataset may be the logarithm of the size.

When the ML model is trained using the logarithm of the size, during inference, the logarithm of the size obtained as an outcome of the ML model in response to an input of a target image is converted to a size (i.e., standard numerical value), by using a set exponentiation base raised to the power of the logarithm of the size. The exponentiation base may be a set hyper-parameter, that is pre-set before the training process begins and remains constant during training. Different training sessions with different values for the exponentiation base may be run to determine the optimal value for the exponentiation base. The exponentiation base may be different for different size maps generated from different feature maps. A relatively smaller feature map is associated with a relatively larger exponentiation base and a relatively larger feature map is associated with a relatively smaller exponentiation base.

At 308, labels indicating type of the polyp depicted in the respective 2D image are created automatically and/or manually.

Polyp type may be according to standard pathological classifications, for example, adenoma. Polyp types may be exclusionary, for example, non-adenoma.

Polyp type may be based on likelihood of accurate determination, for example, unknown.

Polyp type may be a probability, for example, indicating likelihood of developing malignancy, for example, 25%, 50%, 75%, and other values.

The amount of labels indicating type of polyp are difficult to obtain using standard manual approaches, since such labels require a trained expert to view videos of colonoscopies in order to manually determine the type of polyp. Such experts are in limited supply and/or have limited time, making it difficult or impossible to obtain a sufficient number of labels for training the ML model for accurate inference.

An exemplary approach for semi-automatic labelling by a non-expert is now described, which may be used to obtain the sufficient number of labels for training the ML model for accurate inference. Such approach treats each polyp that was noticed by the user performing the colonoscopy (i.e., expert trained user, such as a gastroenterologist) as a non-adenoma.

Each 2D images and/or bounding box label of the 2D image may be associated with a was-noticed parameter and a was-treated parameter, for example, as metadata. The was-noticed parameter indicates whether the respective polyp was noticed by the user performing the procedure (i.e., which is considered as an expert able to correctly assign manual ground labels). The was-treated parameter indicates whether the respective polyp was removed. The was-noticed and/or was-treated parameters may be Boolean values. The was-noticed and/or was-treated parameters may be automatically assigned based on an automated analysis of the 2D image, and/or manually assigned by a non-expert user that views the colonoscopy videos. The ground truth label indicating type of polyp may be automatically assigned to the value of "non-adenoma" when the was-noticed parameter indicates "true" and the was-treated parameter indicates "false".

Automatic analysis and automatic labelling may be performed using one or more of the following approaches (it is noted that a user may manually create labels by manually performing following the approaches below):

Automatically assigning the was-noticed parameter to true when the respective polyp is approximately in the middle of the 2D image for at least a selected duration of time. This may be based on the assumption that the user performing the colonoscopy noticed the polyp, placed the polyp in the middle of the display for better view, and viewed the polyp for at least the duration of time.

Automatically assigning the was-noticed parameter to false when the in respective polyp does not appear approximately in the middle of the image for at least the selected duration of time. This may be based on the assumption that since the polyp was not placed in the middle for the duration of time, the user performing the colonoscopy did not notice the polyp.

Automatically assigning the was-treated parameter to true when a treatment tool appears in the 2D image while the respective polyp is approximately in the middle of the 2D image. The presence of the treatment tool indicates that the polyp was treated.

Automatically assigning the was-treated parameter to false when no treatment tool appears in the 2D image while the respective polyp is approximately in the middle of the 2D image. The absence of the treatment tool indicates that the polyp was not treated.

At 310, one or more training dataset of multiple records are created.

For training a single ML model to generate outcomes of both the size and type for a polyp (in addition to boundary boxes), each record includes a 2D image(s), and ground truth labels including at least one bounding box enclosing the respective polyp, a size of the polyp and a type of the respective polyp.

For training two ML models, two training dataset may be used. The two training datasets may include overlapping 2D images and bounding boxes. The first training dataset includes the size but not type. The second training dataset includes the type but not size.

At 312, training a machine learning model on the training dataset for generating a target bounding box over a target polyp and at least one of the indication of size and type of the polyp, in response to an input of a target 2D image.

Optionally, training is performed by using a single loss function that simultaneously optimizes a size head portion and a type head portion of the ML model. Using the single loss function may avoid increasing processor (e.g., CPU, GPU) and/or memory usage in comparison to performing separate training using different loss functions. Optionally, during the training the gradient is not calculated for both the size head portion and the type head portion. Instead, the weights of the non active head section (i.e., either the size head portion and the type head portion) are frozen, and the active head section and the active loss at each iteration is alternated.

During training, both ground truth and generated size maps may include the logarithm of the size.

Optionally, training for size is performed with a loss function that includes pixel-wise root mean square error (RMSE) between ground truth size maps and machine learning model generated size maps by considering map pixels correspond to ground truth bounding boxes encompassing respective polyps.

When training is performed for size and for type, training may be performed for type using a divergence metric.

At 314, features described with reference to 302-312 may be iterated, for example, using new sample images, to update and/or retrain the ML model.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant ML models will be developed and the scope of the term ML model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of generating instructions for presenting a graphical user interface (GUI) for dynamically evaluating at least one polyp in a plurality of endoscopic images of a colon of a subject, comprising:
    feeding at least one 2D image of an internal surface of a colon captured by an endoscopic camera located within a lumen of the colon, into a machine learning model, wherein the at least one 2D image excludes a depiction of an external measurement tool,
    wherein the machine learning model is trained on a training dataset of a plurality of records, each record including 2D images of the internal surface of the colon of a respective subject labelled with ground truth labels of respective bounding boxes enclosing respective polyps and at least one of an indication of size and a type of the respective polyp indicating likelihood of developing malignancy;
obtaining as an outcome of the machine learning model, a bounding box for a polyp and at least one of an indication of size and type of the polyp; and
generating instructions for presenting within the GUI, an overlay of the bounding box over the polyp and the at least one of the indication of size and type of the polyp, wherein the indication of size comprises a scalar value, further comprising converting the scalar value to a range computed to cover a selected percentage of ground truth sizes in the training dataset.

2. The method of claim 1, further comprising evaluating the at least one of the indication of size and type of the polyp using a set of rules, and generating instructions within the GUI for at least one of: removal of the polyp, tool and/or removal approach for removal of the polyp, and leaving the polyp in situ.

3. The method of claim 1, further comprising excising the polyp when the at least one of the indication of size and type of the polyp meets a set of rules.

4. The method of claim 1, further comprising feeding the overlay of the bounding box over the polyp and the at least one of the indication of size and type of the polyp into a treatment machine learning model to obtain an outcome indicating whether the polyp is to be removed or left in situ, the treatment machine learning model trained on a training dataset that includes multiple records, each record including a respective outcome of a sample bounding box over a sample polyp and the at least one of the indication of size and type of the sample polyp obtained from the machine learning model in response to a sample at least one 2D image, labelled with a ground truth indicating whether the sample polyp was removed or left in situ.

5. The method of claim 1, wherein the machine learning model computes a plurality of feature maps for each 2D images, and generates a plurality of size maps for the plurality of feature maps, each respective size map including at least one 1-dimensional vector representing a logarithm of the estimated size of the polyp, wherein the logarithm of the estimated size is converted to the size using an exponentiation base that is an adjustable hyperparameter, wherein the exponentiation base is set to different values for different size maps computed from different feature maps, wherein the smaller the feature map the larger the exponentiation base.

6. The method of claim 1, wherein the machine learning model is implemented as a neural network, comprising a feature extractor component, a box coordinate network component, a confidence network component, and at least one of a size estimation component and a polyp type estimation component,
wherein the feature extractor component generates a plurality of features maps in response to an input of an image,
wherein the box coordinate network component generates coordinate maps indicating coordinates of candidate bounding boxes when applied to each respective feature map,
wherein the confidence network component generates confidence maps indicating an estimated probability of a respective pixel being a detected polyp when applied respectively to each feature map,
wherein the size estimation component generates size maps indicating an estimated polyp size when applied to each respective feature map,
wherein the polyp type estimation component generates polyp type maps indicating a polyp type when applied to each respective feature map,
wherein the bounding box is obtained by stacking the coordinates maps, the confidence maps, the size maps, and the polyp type maps.

7. The computer implemented method of claim 1, further comprising:
feeding a plurality of 2D images into the machine learning model to obtain a plurality of bounding boxes and a plurality of indications of size and/or type;
identifying a sequence of overlap between the plurality of bounding boxes;
obtaining the plurality of indications of size and/or type over a selected time interval;
removing outlier indications;
averaging the plurality of indications of size and/or type to obtain a single size and/or single type;
iterating the feeding, the identifying, the obtaining, the removing and the average, to obtain a scalar value for a next single size and/or type;
when the scalar value for the next single size and/or type is higher by a margin than a previously computed single size and/or single type, selecting the higher scalar value as the outcome.

8. The computer implemented method of claim 1, wherein feeding comprises sequentially feeding a plurality of 2D images into the machine learning model to obtain a plurality of bounding boxes and indication of size and/or type of the polyp, and switching the size and/or type of the polyp from a previous value to a new value when a number of consecutive bounding boxes above a predefined threshold are associated with the new value.

9. The computer implemented method of claim 1, wherein feeding comprises sequentially feeding a plurality of 2D images into the machine learning model to obtain a plurality of bounding boxes and indication of size and/or type of the polyp, and further comprising:
generating a plurality of records for the plurality of 2D images, each record of each respective 2D image including coordinates of the respective bounding box, a unique box ID assigned for each box associated with each unique polyp, a last seen parameter identifying a frame ID of a last 2D image of the plurality of 2D images where the unique box ID last appeared,
wherein in response to a new unique box ID of a new box of a new 2D image:
searching for at least one record of a previous box that overlaps with the new box by having an intersection over union (IoU) less than a threshold;
setting the unique box ID of the new box to the value of the unique box ID of the previous box that overlaps with the new box;
when no record is found in the search, assigning a new value to the unique box ID of the new box;
removing records that have an overlapping box in the new 2D image, and creating new records for boxes of the new 2D image;
removing records for which the last seen parameter is smaller than the frame ID of the new 2D image by a predefined constant.

10. The computing implemented method of claim 9, wherein the at least one record of the previous box that overlaps with the new box is found when at least one of: (i)

the previous box overlaps with the new box by having an intersection over union (IoU) less than a threshold, and (ii) tracking each box in the plurality of records and comparing new boxes against a tracked value of the boxes in the plurality of records, wherein the tracked values are computed by a tracking process that is fed an input of a current image, a bounding box of a polyp depicted in the current image, and a subsequent next image, and generates an outcome of an estimate of the bounding box for the polyp on the next frame, wherein the tracking value indicates an adjustment of coordinates of the bounding box of a current frame for the next frame.

11. The computer implemented method of claim 9, wherein the at least 2D image is fed into a first machine learning model that generates a first bounding box over the polyp and the indication of size and into a second machine learning model that generates a second bounding box over the polyp and the indication of type, the first and second machine learning models running on a first processor, finding overlapping first and second bounding boxes having an IoU below a threshold by the first processor, and providing one of the first and second bounding boxes that are overlapping to a second processor for creation of the plurality of records.

12. The computer implemented method of claim 11, further comprising designating a dominant machine learning model and a non-dominant machine learning model from the first and second machine learning models, running the dominant machine learning model on the first processor and providing the bounding box outcome of the dominant machine learning model to the second processor, and in parallel running the non-dominant machine learning model and the identifying on the first processor, and providing the one of the first and second bounding boxes to the second processor.

13. The computer implemented method of claim 1, wherein the range is a half-open range when insufficient ground truth is available in the training dataset to obtain an accurate estimation above a threshold.

14. The computer implemented method of claim 1, wherein generating instructions comprises presenting the indication of size and/or type external to borders of the 2D image.

15. The computer implemented method of claim 1, wherein when two or more different bounding boxes are generated for a single 2D image, the indication of size and/or type is presented for a single bounding box closest to a center of the single 2D image, and no indication of size and/or type is presented for other boxes located further away from the center than the single bounding box.

16. The computer implemented method of claim 1, wherein generating instructions comprises presenting the bounding box with a color and/or border style by applying a set of rules to the indication of size and/or type.

17. The computer implemented method of claim 1, wherein generating instructions comprises presenting the bounding box with one of: a first color when the type is adenoma, a second color when the type is non-adenoma, and a third color when the type is unknown.

18. The computer implemented method of claim 1, wherein generating instructions comprises presenting the bounding box with a color hue according to estimated probability of type.

19. The computer implemented method of claim 1, further comprising:
obtaining the at least one 2D image by a local device connected to the endoscopic camera;
transmitting the at least one 2D image by the local device to a server over a network,
wherein the feeding, the obtaining, and the generating instructions are performed by the server; and
presenting on a local display associated with the endoscopic camera, the overlay within the GUI according to the instructions generated by the server and transmitted over the network.

20. A computer implemented method for training a machine learning model for polyp detection, comprising:
creating a training dataset including a plurality of records, each record including a 2D image of a respective internal surface of a respective colon of a respective subject captured by an endoscopic camera located within a respective lumen of the respective colon, and at least one ground truth labels including at least one bounding box enclosing the respective polyp and at least one of the size and a type of the respective polyp indicating likelihood of developing malignancy,
wherein each record of the training dataset includes ground truth labels for the size and type of the respective polyp; and
training a machine learning model on the training dataset for generating a target bounding box over a target polyp and at least one of the indication of size and type of the polyp, in response to an input of a target 2D image,
wherein the machine learning model includes a size head portion and a type head portion, and during training a single loss function that optimizes the size head portion and the type head portion simultaneously is used.

21. The computer implemented method of claim 20, further comprising computing, a logarithm of the size of the respective polyp, wherein the size included in the records of the training dataset comprises the logarithm of the size.

22. The computer implemented method of claim 20, further comprising, in response to obtaining a plurality of target bounding boxes in response to feeding a plurality of target 2D images into the machine learning model, converting the logarithm of the size to a size, by using a set exponentiation base raised to the power of the logarithm of the size.

23. The computer implemented method of claim 22, wherein the exponentiation base is a set hyper-parameter, the exponentiation base is different for different size maps generated from different feature maps, wherein a relatively smaller feature map is associated with a relatively larger exponentiation base and a relatively larger feature map is associated with a relatively smaller exponentiation base.

24. The computer implemented method of claim 20, wherein 2D images of the records are further associated with a was-noticed parameter indicating whether the respective polyp was noticed by the user performing the procedure and a was-treated parameter indicating whether the respective polyp was removed, and automatically assigning the ground truth label indicating type of polyp to non-adenoma when the was-noticed parameter indicates true and the was-treated parameter indicates false.

25. The computer implemented method of claim 24, at least one of: (i) automatically assigning the was-noticed parameter to true when the respective polyp is approximately in the middle of the 2D image for at least a selected duration of time, (ii) automatically assigning the was-noticed parameter to false when the respective polyp does not appear approximately in the middle of the image for at least the selected duration of time, (iii) automatically assigning the was-treated parameter to true when a treatment tool appears in the 2D image while a respective polyp is approximately in the middle of the 2D image, and (iv) automatically assigning the was-treated parameter to false when no treatment tool appears in the 2D image while the respective polyp is approximately in the middle of the 2D image.

26. The computer implemented method of claim 20, wherein the indication includes size, and training for size is performed with a loss function that includes pixel-wise root mean square error (RMSE) between ground truth size maps and machine learning model generated size maps by considering map pixels correspond to ground truth bounding boxes encompassing respective polyps, wherein during training the ground truth and size maps include a logarithm of the size.

27. The computer implemented method of claim 26, wherein the indication further includes type, and training is performed for size and for type, wherein training is performed for type using a divergence metric.

28. A system for dynamically evaluating at least one polyp in a plurality of endoscopic images of a colon of a subject, comprising:
at least one local device comprising:
a first interface for connecting to an endoscopic camera;
a second interface for connecting to a server; and
at least one processor executing a code for obtaining at least one 2D image of an internal surface of a colon captured by the endoscopic camera located within a lumen of the colon, transmitting the at least one 2D image to the server over a network, receiving an indication of an overlay denoting at least one of: detection of at least one polyp, estimation of a size of the at least one polyp, and estimation of a type of the at least one poly, and presenting the overlay on the at least one 2D image on display; and the server comprising:
at least one processor executing a code for:
feeding the at least one 2D image into a machine learning model,
wherein the at least one 2D image excludes a depiction of an external measurement tool,
wherein the machine learning model is trained on a training dataset of a plurality of records, each record including 2D images of the internal surface of the colon of the respective subject labelled with ground truth labels of respective bounding boxes enclosing respective polyps and at least one of an indication of size and a type of the respective polyp indicating likelihood of developing malignancy;
obtaining as an outcome of the machine learning model, at least one bounding box indicating the detection of the at least one polyp and at least one of an indication of size and type of the at least one polyp; and
generating instructions for presenting within the GUI, the overlay of the bounding box over the at least one polyp and the at least one of the indication of size and type of the at least one polyp, wherein the indication of size comprises a scalar value, and
converting the scalar value to a range computed to cover a selected percentage of ground truth sizes in the training dataset.

29. The system of claim 28, wherein the machine learning model is trained on a central computing device, and copies of the machine learning model when trained are distributed to each of a plurality of servers for inference of 2D images obtained from respective associated local devices.

* * * * *